US006177409B1

(12) United States Patent
Vanlemmens et al.

(10) Patent No.: US 6,177,409 B1

(45) Date of Patent: Jan. 23, 2001

(54) METHOD FOR THE SITE SPECIFIC SYNTHESIS OF NOVEL 3-HYDROXYPYRIDIN-4(1H)ONS DERIVATIVES FROM AMINOMONOSACCHARIDES OR AMINOITOLS, PRODUCTS OBTAINED BY THIS METHOD AND THEIR APPLICATIONS

(75) Inventors: Pierre Paul Vanlemmens; Denis Ghislain Postel, both of Amiens; Pierig Emmanuel Germain, Pont Remy; René Jean-Marie Julien, Antony; Jean-Pierre Constant Petit, Amiens; Gino Lino Ronco, Amiens; Pierre Joseph Villa, Amiens, all of (FR)

(73) Assignee: Instituto Biochimico Pavese Pharma S.p.A., Pavia (IT)

( * ) Notice: Under 35 U.S.C. 154(b), the term of this patent shall be extended for 0 days.

(21) Appl. No.: 09/214,134

(22) PCT Filed: Jul. 4, 1997

(86) PCT No.: PCT/FR97/01211

§ 371 Date: Jun. 21, 1999

§ 102(e) Date: Jun. 21, 1999

(87) PCT Pub. No.: WO98/01458

PCT Pub. Date: Jan. 15, 1998

(30) Foreign Application Priority Data

Jul. 5, 1996 (FR) ........................ 96 08382

(51) Int. Cl.[7] .................. A61K 31/70; C07H 19/02; C07D 211/70

(52) U.S. Cl. .................. 514/43; 514/23; 514/345; 536/17.3; 536/22.1; 546/314; 568/852

(58) Field of Search .................. 514/23, 42, 43, 514/345; 536/18.7, 17.3, 22.1; 568/852; 546/242, 314

(56) References Cited

PUBLICATIONS

Al–Refaie et al., "Efficacy and Possible Adverse Effects of the Oral Iron Chelator 1,2–Dimethyl–3–Hydroxypyrid–4–One (L1) in Thalassemia Major", Blood, vol. 80, No. 3, pp. 593–599, Aug. 1992.*

Fassos et al., "Urinary iron excretion depends on the mode of administration of the oral iron chelator 1,2–dimethyl–3–hydroxypyrid–4–one in patients with homozygous beta–thalassemia", Clinical Pharmacology & Therapeutics, vol. 55, No. 1, pp. 70–75, 1994.*

El–Khadem, Hassan. "Carbohydrate Chemistry", published by Academic Press, Inc., pp. 19 and 24, 1988.*

Collins, Peter M. and Robert J. Ferrier. "Monosaccharide", published by John WIley & Sons, p. 18, 1995.*

Kontoghiorges G. J. et al., Lancet, 1294–1295, Jun. 6, 1987.

Hershko C. et al., Ann. N.Y. Acad. Sci., 612, 315–360 (1990).

Marquez et al., J. Med. Chem., 27 (2), 160–164 (1984).

Liu G. et al., Nucleosides, Nucleotide, 14(9–10), 1901–1904 (1995).

* cited by examiner

*Primary Examiner*—Howard C. Lee

(74) *Attorney, Agent, or Firm*—Hedman, Gibson & Costigan, P.C.

(57) ABSTRACT

Process for regiospecific preparation of new 3-hydroxypyridine-4(1H)-one derivatives starting from monosaccharides or itols of general formula:

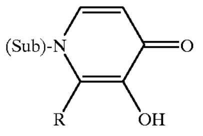

in which R represents a radical, either saturated or not, branched or not, having carbon-atom groups, and having hetero-atoms or not, and Sub represents a saccharide derivative or an itol, either cyclic not, protected or not, the hydrocarbon skeleton of which is bound to the nitrogen atom of the pyridinone either directly or by the intermediary of a spacing group. The present invention is characterized in that the process comprises a first step of protection of the 3-hydroxy group of the pyranone derivative, a second baso-catalyzed step of substitution of the intracyclic oxygen atom of the pyranone by the nitrogen atom of the amine function of the amino monosaccharide or amino itol, and a third step of de-protection of the 3-OH group of the pyridinone cycle and possibly of the OH groups of the glucide or itol residue. It also regards the products obtained by this process, as well as their applications, namely as medicaments for the treatment of toxic overloads of $Fe^{III}$.

19 Claims, 9 Drawing Sheets

Variation of OD as a function of Rv for 1.2-dimethyl-3-hydroxypyridine-4(*1H*)-one (L1)

Calculation of the straight line

Variation of OD as a function of Rv for 1.2-dimethyl-3-hydroxypyridine-4(*1H*)-one (L1) after 1:10 dilution

Calculation of the straight line

Variation of OD as a function of Rv for 2-methyl-3-hydroxypyridine-4(*1H*)-one of solketal

11

Calculation of the straight line

Variation of OD as a function of Rv for 2-methyl-3-hydroxypyridine-4(*1H*)-one of glycerol

14

Calculation of the straight line

Variation of OD as a function of Rv for 2-methyl-3-hydroxypyridine-4(*1H*)-one of glycerol after 1:10 dilution

14

Calculation of the straight line

Variation of OD as a function of Rv for 2-methyl-3-hydroxypyridine-4(*1H*) of mono-acetone xylose

12

Calculation of the straight line

Variation of OD as a function of Rv for 2-methyl-3-hydroxypyridine-4(*1H*)-one of diacetone xylitol

10

Calculation of the straight line

Variation of OD as a function of Rv for 2-methyl-3-hydroxypyridine-4(*1H*)-one of xylitol

17

Calculation of the straight line

Variation of OD as a function of time

Sample: 2-methyl-3-hydroxypyridine-4(*1H*)-one of solketal

λ analysis = 500 nm

Rv = 0.6

* R = V(ligand)/$VFeCl_3$

METHOD FOR THE SITE SPECIFIC SYNTHESIS OF NOVEL 3-HYDROXYPYRIDIN-4(1H)ONS DERIVATIVES FROM AMINOMONOSACCHARIDES OR AMINOITOLS, PRODUCTS OBTAINED BY THIS METHOD AND THEIR APPLICATIONS

This application is a Section 371 application of PCT/FR/97/01211, filed Jul. 4, 1997.

The present invention refers to a process for regiospecific preparation of new 3-hydroxypyridine-4(1H)-one derivatives starting from monosaccharides or itols.

It also regards the products obtained by this process, as well as their applications, namely as complexing agents of $Fe^{III}$.

It is known that the compounds of the 3-hydroxypyridine-4(1H)-one type complex iron in the oxidation state III. These compounds are used, namely, in treatments on humans aimed at limiting forms of $Fe^{III}$ toxic overload (Kontoghiorghes G. J. et al., *Lancet*, 1294–1295 (1987)). Such forms of toxic overload may be of endogenous origin, such as those found in patients affected by siderosis, or exogenous, as in the case of intoxications induced by the massive and frequent polytransfusions to which patients suffering, in particular, from β-thalassaemia are subjected.

It is likewise well known that the toxicity of these compounds for man is less when the -2 site of the pyridine cycle is substituted by an alkyl group, and this without modifying its chelating power in regard to $Fe^{III}$ (Hershko C. et al., *Ann. N.Y. Acad. Sci.*, 612, 351–360 (1990)).

Marquez et al. prepared glycoside derivatives of 2-methyl-3-hydroxypyridine-4(1H)-one by condensation of the benzylated maltol on D-ribose and D-arabinose. activated anomerically in the form of acetate, and of which the other hydroxylated groups are protected in the form of a benzoate or acetate (Marquez et al., *J. Med. Chem.*, 27 (2), 160–164 (1984)).

Using the same strategy, Miller et al. prepared two ribosides of 2-methyl- and 2-ethyl-3-hydroxypyridine-4(1H)-one of configuration β, by reacting 1-trimethylsilyl-2-alkyl-3-benzylpyridine-4(1H)-one on the 1,2,3,4-tetra-O-acetyl-β-D-ribopyranose and the 1-O-acetyl-2,3,5-tri-O-benzoyl-β-D-ribofuranose in the presence of $SnCl_4$ (Liu G. et al., *Nucleosides, Nucleotide*, 14 (9–10), 1901–1904 (1995)).

One of the aims of the present invention is to describe a process for regiospecific synthesis of new 3-hydroxypyridine-4(1H)-one derivatives starting from amino monosaccharides or amino itols of general formula:

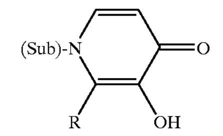

in which R represents an alkyl or alkylene or halo-alkyl or halo-alkylene radical, the halogens being preferably chosen from among chloride and fluoride, linear or branched, having from 1 to 4 carbon atoms and having hetero-atoms or not, and Sub represents a saccharide derivative, either cyclic or not, protected or not, chosen, for example, from among hexose, pentose, and preferably from among glucose, galactose, mannose, fructose, and xylose, or else an itol, either cyclic or not, protected or not, chosen, for example, from among hexitol, pentitol, tetritol or glycerol, and preferably from among glucitol, galacitol, mannitol, xylitol, erythritol, and glycerol, the hydrocarbon skeleton of which is bound to the nitrogen atom of the pyridinone either directly or by the intermediary of a spacing group of an alkylene or halo-alkylene type, the halogen being preferably chosen from among chloride and fluoride, linear or branched, having from 1 to 4 carbon atoms, and hetero-atoms or not.

Figure 1:
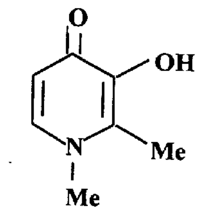
FIG. 1 represents the variation of OD as a function of Rv for 1,2-dimethyl-3-hydroxypyridine-4(1H)-one (L1) by a UV spectrophotometric method.
Figure 1:
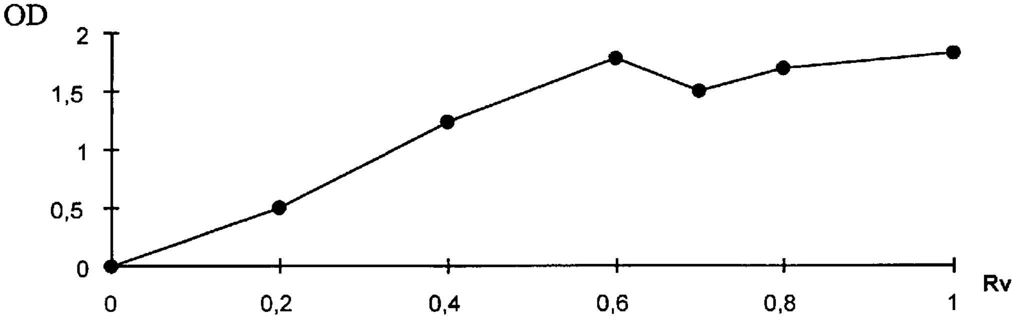
Figure 1:
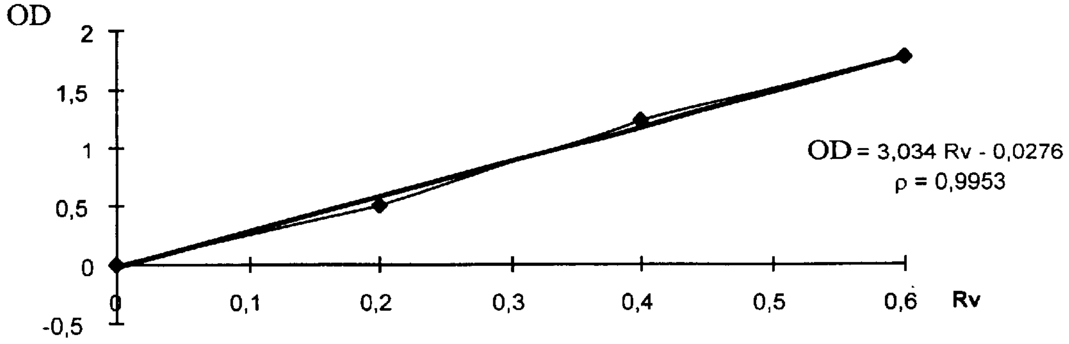
Figure 2:
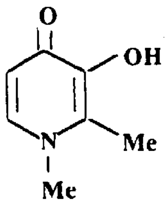
FIG. 2 represents the variation of OD as a function of Rv for 1,2-dimethyl-3-hydroxypyridine-4(1H)-one(L1) after 1:10 dilution.
Figure 2:
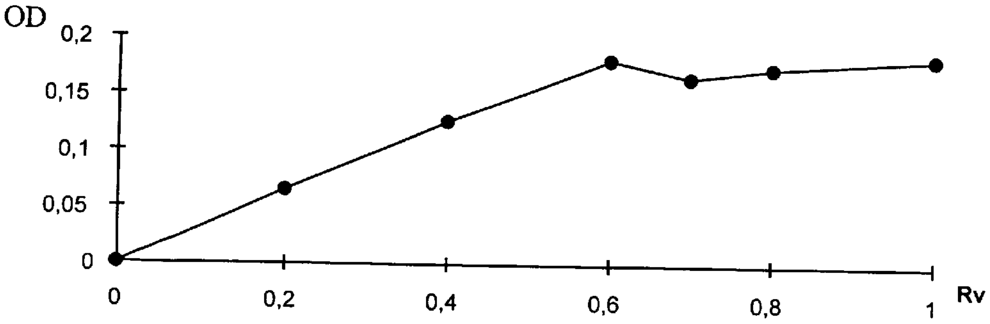
Figure 2:
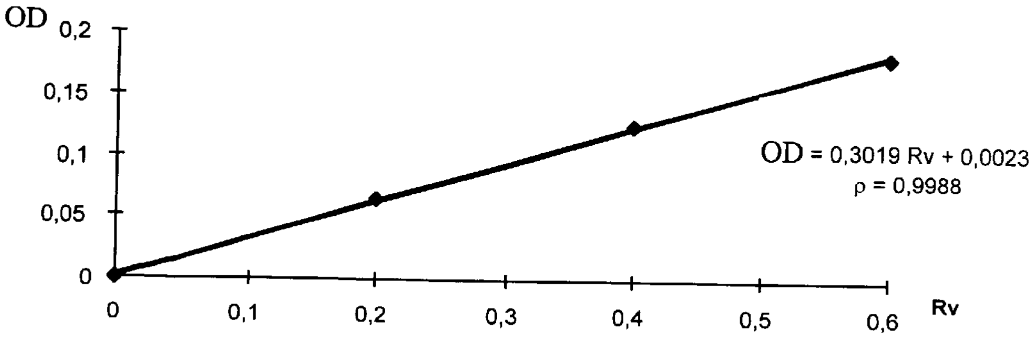
Figure 3:
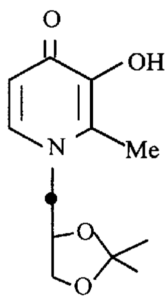
FIG. 3 represents the variation of OD as a function of Rv for 1,2-dimethyl-3-hydroxypyridine-4(1H)-one of solketal.
Figure 3:
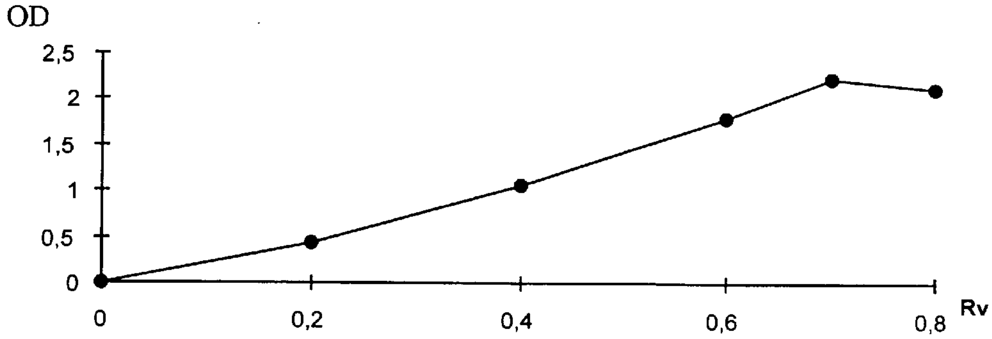
Figure 3:
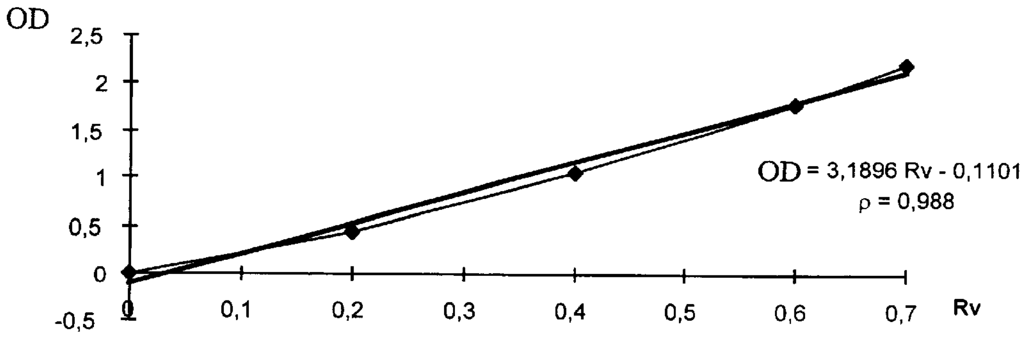
Figure 4:
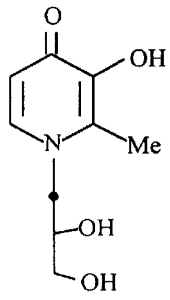
FIG. 4 represents the variation of OD as a function of Rv for 1,2-dimethyl-3-hydroxypyridine-4(1H)-one of glycerol.
Figure 4:
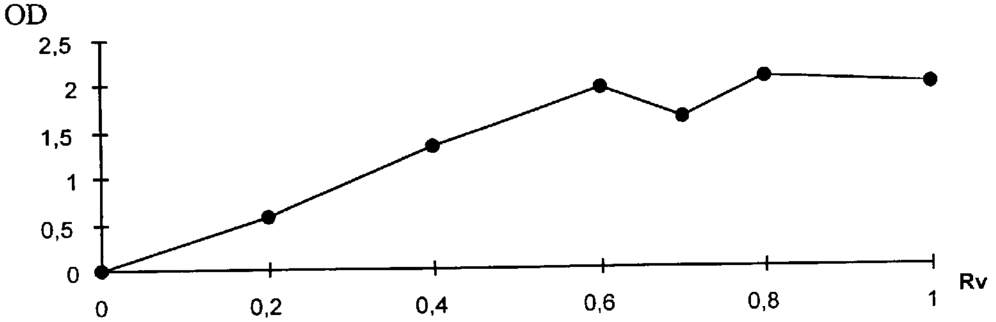
Figure 4:
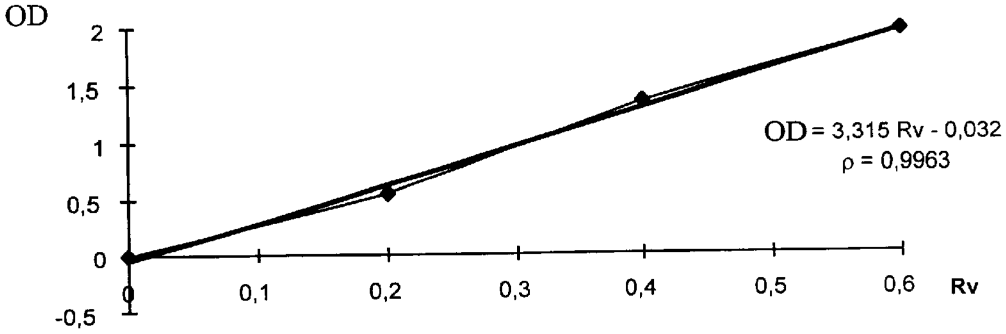

The present invention is characterized in that the process comprises the following steps:

- a first step (step a) of protection of the 3-hydroxy group of the pyranone derivative;
- a second step (step b) of substitution of the intracyclic oxygen atom of the pyranone by the nitrogen atom of the amine function of the amino monosaccharide or amino itol, to obtain the 2-R-3-hydroxypyridine-4(1H)-one derived from the monosaccharide or itol;
- a third step (step c) of de-protection of the 3-OH group of the pyridinone cycle and possibly of the OH groups of the glucide or itol residue.

The OH groups of the glucide residue may possibly also be de-protected in a fourth step (step d).

Step a:

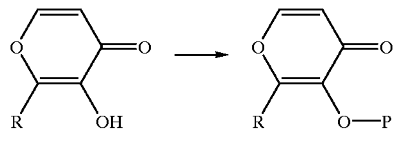

In step (a) of protection of the 3-hydroxy group of the pyranone derivative, the 2-R-3-hydroxypyran-4-one derivative is made to react with at least one molar equivalent of the P-X derivative, where P represents an alkyl group, either cyclic or not, branched or not, saturated or not, or else a phenyl group, either substituted or not, or else an aryl group, either substituted or not, and preferably chosen from among allyl, benzyl, and phenyl, and X is a leaving group chosen, for example, from among halide and sulphonate, and preferably chosen from among chloride, bromide, iodide, tosylate, mesylate, brosylate, nosylate, and triflate. Step (a) of protection is carried out in the presence of at least 1 molar equivalent of a strong base chosen, for example, from among hydroxylated bases, or else from among alcanoates and weak acid salts, where the cation may be monovalent, such as $Na^+$, $K^+$, $Li^+$, $Rb^+$, $Cs^+$, etc., or else an $M^{n+}$ polyvalent cation of the alkaline-earth type, or any other. It is possible to use, as reaction solvent, hydro-alcanolic mixtures, the alcanol being chosen, for example, from among methanol, ethanol, propanol or isobutanol, or else an alcanol alone, or else a polar aprotic solvent chosen, for example, from among hexamethyl phosphorotriamide (HMPA), dimethyl formamide (DMF), dimethoxyethane (DME), dimethyl sulphoxide (DMSO), and acetone, or else a mixture of these; the polar aprotic solvent may be associated or not with an apolar aprotic solvent chosen, for example, from among the aromatic solvents, hydrocarbons, or else ether oxides, or else a mixture of these solvents.

In addition, step (a) comprises the following operations:

elimination of the solvent and retake-up of the residue by an organic solvent;

subsequent washing of the organic phase with a basic aqueous solution as defined previously, and then with water;

evaporation of the organic phases obtained previously to arrive to the pyranone derivative protected in -3.

Step b:

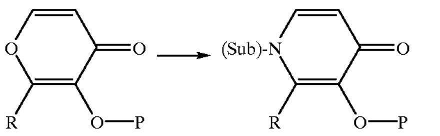

In step (b) of substitution of the intracyclic oxygen atom of the pyranone by the nitrogen atom of the amino monosaccharide or amino itol, at least 1 molar equivalent of the protected pyranone obtained in step (a) is made to react in the presence of a strong base, as defined in step (a), on 1 molar equivalent of the amino monosaccharide or amino itol, carrying the amino group either directly onto the saccharide residue or by the intermediary of a spacing group.

The amino saccharides and the amino itols are obtained in the classic conditions described in the literature, consisting in the direct condensation of ammonia on an activated monosaccharide or itol (Fletchner T. W., *Carbohydr. Res.*, 77, 262 (1979)), or else consisting in the preparation of azide derivatives of monosaccharide or itol, followed by the reduction into amino derivatives by catalytic hydrogenation or by a metal hydride (Scriven E. F. V., *Chem. Reviews*, 88, 2 (1988)), or else PPh3-H20 (Mungall W. S. et al., *J. Org. Chem.*, 40, 11 (1975)).

As solvent of step (b), it is possible to use hydro-alcanol mixtures, the alcanol being chosen, for example, from among methanol, ethanol, propanol, and isobutanol, or else an alcanol alone, or else a polar aprotic solvent chosen, for example, from among hexamethyl phosphorotriamide (HMPA), dimethyl formamide (DMF), dimethoxyethane (DME), dimethyl sulphoxide (DMSO), acetone, or else a mixture of these. The polar aprotic solvent may be associated or not to an apolar aprotic solvent chosen, for example, from among the aromatic solvents, hydrocarbons, or else ether oxides, or else a mixture of these solvents.

Furthermore, step (b) comprises the following operations:

neutralization of the base by addition of a mineral or organic acid;

elimination of the organic solvent;

retake-up of the residue by an organic solvent and washing of the organic phase with water;

evaporation of the organic phase;

purification of the residue by re-crystallization or chromatography.

Step c:

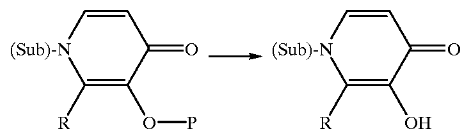

Step (c) consists in the de-protection of the pyridinone cycle of the compounds obtained from step (b). According to the nature of the protective groups P introduced in step (a), the de-protection may be performed by hydrogenolysis, for example, for P chosen from among benzyl, phenyl and allyl, or else, for example, when P is an allyl group, by acidocatalyzed hydrolysis, after basocatalyzed isomerization of the allyl group into a propenyl group.

As reaction solvent for the de-protection by hydrogenolysis, it is possible to choose an alcanol, or else an alcanol-water mixture, the alcanol being chosen, for example, from among methanol, ethanol, propanol, isopropanol, etc., or else an organic solvent associated or not to water and enabling solubilization of the de-protected product, chosen, for example, from among tetrahydrofran, dioxane, etc.

It is possible to choose Pd/C as hydrogenolysis catalyst, or else any other hydrogenolysis catalyst chosen, for example, from among platinum derivatives, nickel derivatives, etc.

Furthermore, step (c) comprises the following operations:

filtration of the catalyst;

elimination of the organic solvent;

purification of the residue, for example, by re-crystallization, for instance in a binary mixture of organic solvents, chosen, for example, from between hexane and acetone.

Step (c) can advantageously be carried out, in the case of compounds with saccharide residue protected by acido-labile groups, in the conditions described previously in the presence of an acid catalyst, so as to bring about the de-protection of the protecting groups of the saccharide residue using the "one pot" technique. The saccharide derivative of the 2-R-3-hydroxypyridine-4(1H)-one can then be obtained either in the form of ammonium salt, for example, by lyophilization of the reaction medium after elimination of the organic solvent and addition of water, or in the form of amine after neutralization of the reaction medium, for example, by passage over ion-exchange resin having a basic nature, chosen, for instance, from among Dowex®, Amberlyst®, and Amberlite®.

The compounds obtained from step (c) the saccharide residue of which possesses protected hydroxyl groups can undergo step (d) of de-protection of the hydroxyl groups according to the classic conditions described in the literature, chosen on the basis of the nature of the protecting groups themselves.

Another aim of the present invention is to provide new 2-R-3-hydroxypyridine-4(1H)-one derivatives of monosaccharides or itols corresponding to the following formula:

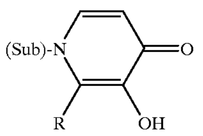

as defined previously, with the exclusion of the arabinose and ribose derivatives that carry the pyranone residue on the anomeric site, which, by their chemical properties, may find application as metal chelating agents, and more in particular, as medicaments for the treatment of $Fe^{III}$ toxic overloads.

A further subject of the present invention is represented by medicaments for the treatment of metal toxic overloads involving a therapeutically effective quantity of at least one compound according to the invention in a vehicle that may be administered to humans. This vehicle may be an ordinary vehicle for oral or intramuscular administration. The medicament is administered either once or a number of times. Preferably, the medicament is prepared in doses of between 30 and 150 mg/kg/day (kg of body weight).

The invention moreover refers to a therapeutic process for the treatment of metal toxic overload in which the medicament according to the invention is administered to the patient.

The treatment is in particular useful in the case of $Fe^{III}$ toxic overload. Among these cases of overload the following may be cited: haemoglobinopathies, β-thalassaemia, and drepanocytosis.

Likewise forming a subject of the present invention is the use of the new compounds according to the invention for the preparation of a medicament for the treatment of the above-mentioned disorders.

FIGS. from 1 to 9 present, for the various compounds, the variation in optical density (OD) according to the Rv ratio (Rv=Volume of solution of Ligand/Volume of solution of $Fe^{III}$).

EXAMPLE 1

Synthesis of 2-methyl-3-benzyloxy-4-pyranone (1)

20.0 g (159 mmol) of 2-methyl-3-hydroxy-4-pyranone and 22.1 g (175 mmol, 1.1 eq.) of benzyl chloride are introduced into 200 mL of methanol; then 6.98 g (175 mmol) of NaOH in 22 mL of water are added. The reaction medium is reflux agitated for 6½ hours. The solvent is subsequently evaporated and the residue retaken up with 100 mL of dichloromethane. This solution is then washed with a 5% aqueous solution of soda (2×80 mL) and with water (2×80 mL). The organic phases are collected, dried on sodium sulphate, filtered and evaporated under reduced pressure; 32.3 g (149 mmol) of 2-methyl-3-benzyloxy-4-pyranone are isolated. Yield: 94%.

1

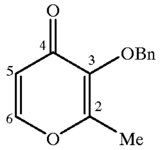

orange oil

Rf = 0.51 (Ph—H—MeOH; 4:1)

NMR $^1H$: δ 8.00 (d, $J_{5,6}$=5.7 Hz, H-6), 7.42–7.30 (m,5H Ph), 6.37 (d, $J_{5,6}$=5.7 Hz, H-5), 5.04 (s, $CH_2$-Ph), 2.10 (s, $CH_3$); NMR $^1H$ in $CDCl_3$: δ 7.55 (d, H-6), 7.40 (s, 5H, aromatic H), 6.35 (d, H-5), 5.04 (s, $CH_2$-Ph), 2.10 (s, $CH_3$); NMR $^{13}C$: δ 173.9 (C-4), 159.1 (C-3), 154.8 (C-6), 143.1 (C-2), 136.6 ($C_{Ipso}$), 128.5 (2×$C_{ortho}$), 128.2 (2×$C_{meta}$), 128.0 ($C_{para}$), 116.4 (C-5), 72.6 ($CH_2$-Ph), 14.3 ($CH_3$).

EXAMPLE 2

Synthesis of 1-(2',3':4',5'-di-O-isopropylidene-xylityl)-2-methyl-3-benzyloxypyridine-4(1H)-one (known as: 2-methyl-3-benzyloxypypyridine-4(1H)-one of diacetone xylitol) (2)

20.0 g (92.5 mmol, 1.5 eq.) of 2-methyl-3-benzyloxy-4-pyranone and 14.3 g (61.8 mmol) of 1-amino-1-desoxy-2,3,4,5-di-O-isopropylidene-xylitol are introduced into 350 mL of a 50:50 ethanol-water mixture. Then, 8 mL of an aqueous solution of soda (2N) are added.

The reaction medium is reflux agitated for 3 days. It is then allowed to cool off and neutralized by adding a solution of concentrated HCl. After evaporation of the ethanol, the residue is extracted by means of a 60:40 v/v dichloromethane-water mixture (400 mL). The organic phases are collected, dried on anhydrous $Na_2SO_4$, filtered, and then evaporated under reduced pressure. The residue is re-crystallized in a hexane-acetone mixture, and 10.2 g (23.7 mmol) of 2-methyl-3-benzyloxypyridine-4(1H)-one of diacetone xylitol is isolated, which is pure at chromatographic and NMR analyses. Yield: 38%.

2

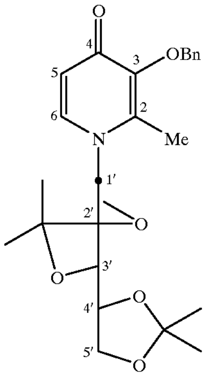

white powder $[\alpha]^{25}_D$ = 1° (c = 1.1; MeOH)

F = 85° C.

Rf = 0.29 (Ph—H—MeOH; 4:1)

NMR $^1H$: sugar; δ 4.23–4.05 (massive, H-1'$_a$, H-1'$_b$, H-2', H-4', H-5'$_a$), 3.84 (dd, $J_{3',4'}$=7.6 Hz, $J_{2',3'}$=7, H-3'), 3.72 (dd, H-5'$_b$), 1.33 (s, $CH_3$), 1.31 (s, $CH_3$), 1.29 (s, $CH_3$), 1.29 (s, $CH_3$); heterocycle: δ 7.54 (d, J5,6=7.6 Hz, H-6), 7.42–7.31 (m, 5H Ph), 6.21 (d, $J_{5,6}$=7.6 Hz H-5), 5.02 (2 dd, $H_a$ $CH_2$-Ph), $H_b$ $CH_2$-Ph), 2.20 (s, $CH_3$); NMR $^{13}C$: sugar; δ 109.4 ($C_{Ip}$), 108.7 ($C_{Ip}$), 77.3 (C-3'), 76.0 (C-2'), 73.8 (C-4'), 64.8 (C-5'), 54.1 (C-1'), 26.7 ($CH_3$), 26.5 ($CH_3$), 25.9 ($CH_3$), 25.3 ($CH_3$); heterocycle: δ 171.9 (C-4), 144.9 (C-2), 141.0 (C-3), 140.0 (C-6), 137.6 ($C_{Ipso}$), 128.4 (2×$C_{ortho}$), 128.1 (2×$C_{meta}$), 127.7 ($C_{para}$), 115.7 (C-5), 71.7 ($CH_2$-Ph), 13.3 ($CH_3$).

EXAMPLE 3

Synthesis of 1-(2',4':3',5'-di-O-methylene-xylityl)-2-methyl-3-benzyloxypyridine-4(1H)-one (known as: 2-methyl-3-benzyloxypyridine-4(1H)-one of dimethylene xylitol) (3)

The 2-methyl-3-benzyloxypyridine-4(1H)-one of dimethylene xylitol is prepared according to the method described in Example 2. Starting from 5.50 g (31.4 mmol) of 1-amino-1-desoxy-dimethylene xylitol compound, after re-crystallization in a hexane-acetone mixture, 5.04 g (13.5 mmol) of 2-methyl-3-benzyloxypyridine-4(1H)-one of dimethylene xylitol is isolated, which is pure at chromatographic and NMR analyses. Yield: 43%.

3

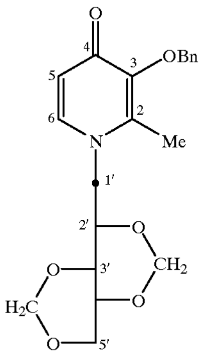

white powder $[\alpha]^{25}_D = 2°$ (c = 1.0; MeOH)

F = 193° C.

Rf = 0.23 (Ph—H—MeOH; 4:1)

NMR $^1H$: sugar: δ 4.99 (dd, $J_{H',H''}$=6.3, $CH_2$), 4.67 (dd, $J_{H',H''}$=6.3, $CH_2$), 4.60–3.60 (massive, H-1', H-2', H-4', H-5', H-3'); heterocycle: δ 7.52 (d, $J_{5,6}$=7.6 Hz, H-6), 7.42–7.31 (m, 5H Ph), 6.14 (d, $J_{5,6}$=7.6 Hz, H-5), 5.01 (m, $CH_2$-Ph), 2.21 (s, $CH_3$); NMR $^{13}C$: sugar: δ 92.0 ($CH_2$), 91.6 ($CH_2$), 75.7 (C-3'), 69.4 (C-2'), 69.4 (C-4'), 66.5 (C-5'), 52.5 (C-1'); heterocycle: δ 171.6 (C-4), 145.0 (C-2), 141.0 (C-3), 140.1 (C-6), 137.7 ($C_{Ipso}$), 128.2 (2×$C_{ortho}$), 128.1 (2×$C_{meta}$), 127.7 ($C_{para}$), 115.6 (C-5), 71.7 ($CH_2$-Ph), 12.1 ($CH_3$).

EXAMPLE 4

Synthesis of 1-(1',2'-O-isopropylidene-α-D-xylofurano-5-yl)-2-methyl-3-benzyloxypyridine-4(1H)-one (known as: 2-methyl-3-benzyloxypyridine-4(1H)-one of mono-acetone xylose) (4)

The 2-methyl-3-benzyloxypyridine-4(1H)-one of diacetone xylose is prepared according to the method described in example 2. Starting from 4.50 g (23.8 mmol) of 5-amino-5-desoxy-mono-acetone xylose compound, after re-crystallization in a dichloromethane-ethyl ether mixture, 3.87 g (9.98 mmol) of 2-methyl-3-benzyloxypyridine-4(1H)-one of mono-acetone xylose is isolated, which is pure at chromatographic and NMR analyses. Yield: 42%.

4

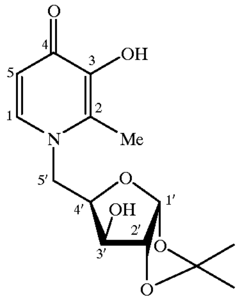

yellow powder $[a]^{25}_D = 54°$ (c = 1.0; MeOH)

F = 177° C.

Rf = 0.30 (Ph—H—MeOH; 4:1)

NMR $^1H$: sugar: δ 5.86 (d, J2',3'=3.2 Hz, H-1'), 4.45 (d,$J_{2',1'}$=3.6 Hz, H-2'), 4.17–3.99 (massive, H-3', H-4', H-5'), 1.34 ($CH_3$), 1.22 (s, $CH_3$); heterocycle: δ 7.60 (d, J5,6=7.5 Hz, H-6), 7.42–7.27 (m, 5H Ph), 6.17 (d, J5,6=7.6 Hz, H-5), 5.02 (2 dd, $H_a$ $CH_2$-Ph), $H_b$ $CH_2$-Ph), 2.20 (s, $CH_3$); NMR $^{13}C$: sugar: δ 110.6 ($C_{Ip}$), 104.3 (C-1'), 84.9 (C-2'), 79.5 (C-3'), 73.5 (C-4'), 51.6 (C-5'), 26.5 ($CH_3$), 25.9 ($CH_3$); heterocycle: δ 171.9 (C-4), 145.0 (C-2), 141.2 (C-3), 139.7 (C-6), 137.7 ($C_{Ipso}$), 128.2 (2×$C_{ortho}$), 128.1 (2×$C_{meta}$), 127.7 ($C_{para}$), 115.9 (C-5), 71.7 ($CH_2$-Ph), 12.2 ($CH_3$).

EXAMPLE 5

Synthesis of the 1-(2',3'-O-isopropylidene-glyceryl)-2-methyl-3-benzyloxypyridine-4(1H)-one (known as: 2-methyl-3-benzyloxypyridine-4(1H)-one solketal) (5)

The 2-methyl-3-benzyloxypyridine-4(1H)-one of solketal is prepared according to the method described in example 2. Starting from 5.00 g (38.1 mmol) of the 1-amino-1-desoxy solketal compound, after silica gel chromatography with a mixture of acetone-TEA-ethanol 80:10:10 v/v/v, 5.26 g (15.9 mmol) of 2-methyl-3-benzyloxypyridine-4(1H)-one of solketal is isolated, which is pure at chromatographic and NMR analyses. Yield: 42%.

5

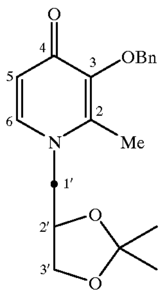

yellow powder $[\alpha]^{25}_D = 2°$ (c = 1.0; MeOH)

F = 55° C.

Rf = 0.32 (Ph—H—MeOH; 4:1)

NMR $^1H$: sugar: δ 4.25 (m, H-2'), 4.15–3.89 (massive, H-1'$_a$, H-1'$_b$, H-3'), 3.59 (dd, J2',3=6.4 Hz, 1.30 (s, $CH_3$), 1.24 (s, $CH_3$); heterocycle: δ 7.55 (d, J5,6=7.4 Hz, H-6), 7.42–7.32 (m, 5H Ph), 6.16 (d, J5,6=7.6 Hz, H-5), 5.02 (2 dd, $H_a$ $CH_2$-Ph), $H_b$ $CH_2$-Ph), 2.19 (s, $CH_3$); NMR $^{13}C$: sugar: δ 109.1 ($C_{Ip}$), 74.4 (C-2'), 65.7 (C-3'), 54.6 (C-1'), 26.2 ($CH_3$), 25.1 ($CH_3$); heterocycle: δ 171.9 (C-4), 144.9 (C-2), 141.1 (C-3), 140.0 (C-6), 137.6 ($C_{Ipso}$), 128.3 (2×$C_{ortho}$), 128.1 (2×$C_{meta}$), 127.7 ($C_{para}$), 115.6 (C-5), 71.7 ($CH_2$-Ph), 12.3 ($CH_3$).

EXAMPLE 6

Synthesis of the 1-(1',2':3',4'-di-O-isopropylidene-α-D-galactopyranose-6-yl)-2-methyl-3-benzyloxypyridine-4(1H)-one (known as: 2-methyl-3-benzyloxypyridine-4(1H)-one of diacetone galactose) (6)

The 2-methyl-3-benzyloxypyridine-4(1H)-one of diacetone galactose is prepared according to the method described in example 2. Starting from 2.5 g (9.64 mmol) of 6-amino-6-desoxy diacetone galactose, after silica gel chromatography with a mixture of acetone-water 90:10 v/v, 2.03 g (4.42 mmol) of 2-methyl-3-benzyloxypyridine-4(1H)-one of diacetone galactose is isolated, which is pure at chromatographic and NMR analyses. Yield: 46%.

6

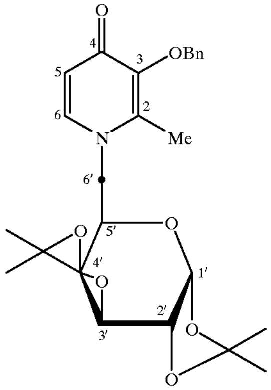

brown powder $[\alpha]^{25}_D$ = -65° (c = 0.5; MeOH)

F = 95° C.

Rf = 0.56 (Ph—H—MeOH; 4:1)

NMR $^1$H: sugar: δ 5.40 (d, $J_{1',2'}$=5.0 Hz, H-1'), 4.63 (dd, $J_{3',4'}$=5.6 Hz, (dd, $J_{4',5'}$=2.36 Hz, H-4'), 4.27 (dd,J2',3'=2.19 Hz, H-2'), 4.15 (m, H-6'$_a$), 3.96 (m, H-5'), 3.84 (dd,$J_{6'a,6'b}$= 14.6 Hz, H-6'$_b$), 1.38 ($CH_3$), 1.30 (s, 2×$CH_3$), 1.21 (s, $CH_3$); heterocycle: δ 7.63 (d, J5,6=7.5 Hz, H-6), 7.42–7.30 (m, 5H, Ph), 6.16 (d, J5,6=7.6 Hz, H-5), 4.99 (2 dd, $J_{Ha,Hb}$=11.1, $H_a$ CH2-Ph, $H_b$ CH2-Ph), 2.18 (s, $CH_3$); NMR $^{13}$C: sugar: δ 108.7 ($C_{Ip}$), 107.9 ($C_{Ip}$), 95.5 (C-1'), 70.3 (C-2'), 70.1 (C-3'), 69.6 (C-4'), 67.2(C-5'), 52.2 (C-6'), 25.9 ($CH_3$), 25.6 ($CH_3$), 24.6 ($CH_3$), 24.2 ($CH_3$); heterocycle; δ 171.9 (C-4), 144.9 (C-2), 141.2 (C-3), 139.7 (C-6), 137.7 ($C_{Ipso}$), 128.2 (2×$C_{ortho}$), 128.0 (2×$C_{meta}$), 127.7 ($C_{para}$), 115.7 (C-5), 71.8 ($CH_2$-Ph), 12.1 ($CH_3$).

EXAMPLE 7

Synthesis of the 1-(2',3':5',6'-di-O-isopropylidene-α-D-mannofuranoside of but-4-yl)-2-methyl-3-benzyloxypyridine-4(1H)-one (known as: 2-methyl-3-benzyloxypyridine-4(1H)-one of diacetone mannoside of butyl) (7)

The 2-methyl-3-benzyloxypyridine-4(1H)-one of diacetone mannoside of butyl is prepared according to the method described in example 2. Starting from 2.00 g (6.04 mmol) of diacetone mannoside of 4'-aminobutyl, after silica gel chromatography with a mixture of acetone-water 90:10 v/v, 1.72 g (3.25 mmol) of 2-methyl-3-benzyloxypyridine-4(1H)-one of diacetone mannoside of butyl is isolated, which is pure at chromatographic and NMR analyses. Yield: 54%.

7

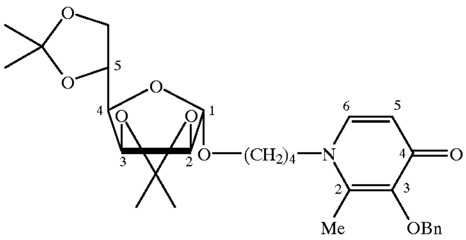

brown syrupy liquid $[a]^{25}_D$ = -38° (c = 0.5 MeOH)

NMR $^1$H: sugar: δ 4.95 (s, H-1'), 4.73 (dd, $J_{3,4}$=3.5 Hz, H-3'), 4.52 (d, $J_{2,3}$5.8 Hz, H-2), 4.26 (dd, J5,6$_a$=6.1 Hz, H-5'), 4.01 (dd, $J_{6a,6b}$=8.4 Hz, J5,6$_b$=6.8 Hz, H-6$_a$), 3.88–3.82 (m, H-6$_b$, H-4',H-4"), 3.54 (dd, $J_{1"a,1"b}$=7.1 Hz, H-1"$_a$), 3.43 (dd, $J_{1"a,2"}$=3.9 Hz, H-1'$_b$), 1.59–1.45 (m, H-2', H-3'), 1.35 (s, $CH_3$), 1.32 (s, $CH_3$), 1.26 (s, $CH_3$), 1.24 (s, $CH_3$); heterocycle: δ 7.56 (d, J5,6=7.4 Hz, H-6), 7.41–7.30 (m, 5H, Ph), 6.14 (d, J5,6=7.5 Hz, H-5), 5.03 (m, $CH_2$-Ph), 2.14 (s, $CH_3$); NMR $^{13}$C: sugar δ 111.5 ($C_{Ip}$), 108.0 ($C_{Ip}$), 105.6 (C-1'), 84.3 (C-2'), 79.7 (C-4'), 78.9 (C-3'), 72.4 (C-5'), 66.0 (C-1"), 65.9 (C-6'), 52.3 (C-4"), 26.9 25.6 (C-2". C-3"), 26.4 ($CH_3$), 25.6 ($CH_3$), 25.0 ($CH_3$), 24.2 ($CH_3$). heterocycle: δ 171.7 (C-4), 145.2 (C-2), 140.3 (C-3), 139.2 (C-6), 137.7 ($C_{Ipso}$), 128.3 (2×$C_{ortho}$), 128.0 (2×$C_{meta}$), 127.6 ($C_{para}$), 115.9 (C-5), 71.6 ($CH_2$-Ph), 11.7 ($CH_3$).

EXAMPLE 8

Synthesis of the 1-glyceryl-2-methyl-3-benzyloxypyridine-4(1H)-one (known as: 2-methyl-3-benzyloxypyridine-4(1H)-one glycerol) (8)

35.6 g (165 mmol. 1.5 eq.) of 2-methyl-3-benzyloxy-4-pyranone and 10 g (110 mmol) of 1-amino-1-desoxy-glycerol are put into 600 mL of a 50:50 ethanol-water mixture; then 14 mL of an aqueous solution of soda (2N) is added. The reaction medium is then brought under reflux agitation for 48 hours. The reaction medium is left to cool, and then a solution of concentrated HCl is added to reach a pH=1. After evaporation of ethanol, the resifue is extracted using ethyl ether (3×100 mL) in order to eliminate any excess of 2-methyl-3-benzyloxy-4-pyranone. The aqueous phase is brought to neutral pH by addition of an aqueous solution of NaOH and then concentrated under reduced pressure. The residue is retaken up with a minimum of water. By precipitation, 12.7 g (43.9 mmol) of 2-methyl-3-benzyloxypyridine-4(1H)-one of glycerol is isolated, which is pure at chromatographic and NMR analyses. Yield 40%.

8

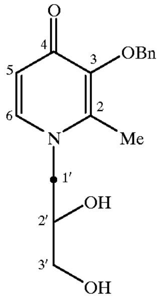

beige powder

F = 80–82° C.

Rf = 0.4 (Ph—$CH_3$—MeOH; 2:1)

NMR $^1$H: sugar: δ3.93 (d,$J_{1'a,1'b}$=12.1 Hz, H-1'$_a$), 3.72 (d, H-1'$_b$), 3.79 (massive, H-2'), 3.48 (m, $H_{3'a}$ $H_{3'b}$); heterocycle: δ 7.38 (d, J5,6=7.15 Hz, H-6), 7.26–7.09 (m, 5H Ph), 6.20 (d, J5,6=7.15 Hz, H-5), 4.93 (d, $J_{Ha,Hb}$=12.1, $H_a$ $CH_2$-Ph), 4.84 (d, $H_b$ $CH_2$-Ph), 2.06 (s, $CH_3$); NMR $^{13}$C: sugar: δ 70.4 (C-2'), 63.8 (C-3'), 56.8 (C-1'); heterocycle: δ 171.9 (C-4), 144.9 (C-2), 141.1 (C-3), 140.0 (C-6), 137.6 ($C_{Ipso}$), 128.8 (2×$C_{meta}$), 128.3 (2×$C_{ortho}$), 128.2 ($C_{para}$), 115.9 (C-5), 73.3 ($CH_2$-Ph), 12.7 ($CH_3$).

EXAMPLE 9

Synthesis of the 1-(2',4':3',5'-di-O-methylene-xylityl)-2-methyl-3-hydroxypyridine-4(1H)-one (known as: 2-methyl-3-hydroxypyridine-4(1H)-one of dimethylene xylitol) (9)

1.00 g (2.68 mmol) of 2-methyl-3-benzyloxypyridine-4 (1H)-one of dimethylene xylitol is put into the mixture of 10 mL ethanol—2 mL $H_2O$, and 0.11 g of Pd/C at 10% is added. The reaction medium is subjected to catalytic hydrogenolysis under agitation at room temperature for 4 hours. At the end of this hydrogenolysis, the reaction medium is filtered. The solution is evaporated under reduced pressure, and after extraction and re-crystallization in a hexane-acetone mixture, 589 mg (2.09 mmol) of 2-methyl-3-hydroxypyridine-4(1H)-one of dimethylene xylitol is isolated, which is pure at chromatographic and NMR analyses. Yield: 78%.

9

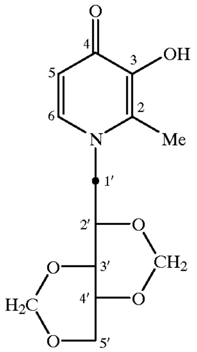

white powder
F = 272° C.
Rf = 0.13 (Ph—H—MeOH; 4:1)

NMR $^1H$: sugar: δ 5.01 (dd, $J_{H',H''}$=6.3, $CH_2$), 4.69 (dd, $J_{H',H''}$=6.3, $CH_2$), 4.16–3.62 (massive, H-1', H-2', H-4', H-5', H-3'); heterocycle: δ 7.48 (d, J5,6=7.3 Hz, H-6), 6.10 (d, J5,6=7.3 Hz, H-5), 2.21 (s, $CH_3$); NMR $^{13}C$: sugar: δ 92.0 ($CH_2$), 91.8 ($CH_2$), 75.9(C-3'), 69.4 (C-2'), 69.4 (C-4'), 68.5 (C-5'), 52.6 (C-1'); heterocycle: δ 170.0 (C-4), 145.1 (C-2), 138.4 (C-6), 128.9 (C-3), 110.3 (C-5), 11.5 ($CH_3$). IR (KBr): 3147, 1627 $cm^{-1}$. UV (MeOH): $\lambda_{max}$=298 nm. log ε=3.04.

EXAMPLE 10

Synthesis of the 1-(2',3':4',5'-di-O-isopropylidene-xylityl)-2-methyl-3-hydroxypyridine-4(1H)-one (known as: 2-methyl-3-hydroxypyridine-4(1H)-one of diacetone xylitol) (10)

The 2-methyl-3-hydroxypyridine-4(1H)-one of diacetone xylitol is prepared according to the method described in example 9. Starting from 1.50 g (3.49 mmol) of 2-methyl-3-benzyloxypyridine-4(1H)-one of diacetone xylitol, after extraction and re-crystallization in the hexane-acetone mixture, 604 mg (1.78 mmol) of 2-methyl-3-hydroxypyridine-4(1H)-one of diacetone xylitol is isolated, which is pure at chromatographic and NMR analyses. Yield: 51%.

10

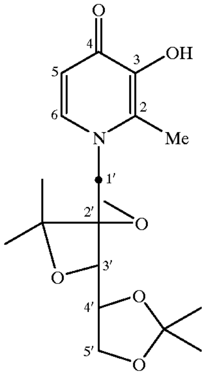

white powder
F = 228° C.
Rf = 0.24 (Ph—H—MeOH; 4:1)

NMR $^1H$: sugar: δ 4.23–4.05 (massive, H-1'$_a$, H-1'$_b$, H-2', H-4', H-5'$_a$), 3.84 (dd, $J_{3',4'}$=7.6, Hz, J2',3'=7, H-3'), 3.72 (dd, H-5'$_b$), 1.33 (s, $CH_3$), 1.31 (s, $CH_3$), 1.29 (s, $CH_3$); heterocycle: δ7.54 (d, J5,6=7.6 Hz, H-6), 7.42–7.31 (m, 5H Ph), 6.21 (d, J5,6=7.6 Hz, H-5), 5.02 (2 dd, $H_a$ $CH_2$-Ph), $H_b$ $CH_2$-Ph), 2.20 (s, $CH_3$); NMR $^{13}C$: sugar: δ 109.4 ($C_{Ip}$), 108.7 ($C_{Ip}$), 77.5 (C-3'), 76.1 (C-2'), 73.9 (C-4'), 64.8 (C-5'), 54.2 (C-1'), 26.7 ($CH_3$), 26.5 ($CH_3$), 25.9 ($CH_3$), 25.3 ($CH_3$); heterocycle: δ 171.9 (C-4), 144.9 (C-2), 141.0 (C-3), 140.0 (C-6), 137.6 ($C_{Ipso}$), 128.4 (2×$C_{ortho}$), 128.1 (2×$C_{meta}$), 127.7 ($C_{para}$), 115.7 (C-5), 71.7 ($CH_2$-Ph), 13.3 ($CH_3$) IR (KBr): 3183, 1626 $cm^{-1}$. UV (MeOH): $\lambda_{max}$=299 nm. log ε=3.04.

EXAMPLE 11

Synthesis of the 1-(2',3'-O-isopropylidene-glyceryl)-2-methyl-3-hydroxypyridine-4(1H)-one (known as: 2-methyl-3-hydroxypyridine-4(1H)-one of solketal) (11)

The 2-methyl-3-hydroxypyridine-4(1H)-one of solketal is prepared according to the method described in example 9. Starting from 1.00 g (3.04 mmol) of 2-methyl-3-benzyloxypyridine-4(1H)-one of solketal, after extraction and re-crystallization in a hexane-acetone mixture, 545 mg (2.28 mmol) of 2-methyl-3-hydroxypyridine-4(1H)-one of solketal is isolated, which is pure at chromatographic and NMR analyses. Yield: 75%.

11

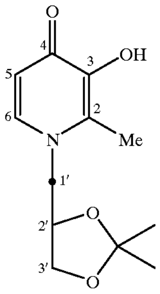

white powder
F = 165° C.
Rf = 0.23 (Ph—H—MeOH; 4:1)

NMR $^1H$: sugar: δ4.30 (m, H-2'), 4.21–3.93 (massive, H-1'$_a$. H-1'$_b$. H-3'$_a$), 3.65 (dd, J2',3'=6.2 Hz), 1.32 (s, $CH_3$), 1.24 (s, $CH_3$); heterocycle: δ 7.55 (d, J5,6=7.4 Hz, H-6), 7.42–7.32 (m, 5H Ph), 6.16 (d, J5,6=7.6 Hz, H-5), 5.02 (2 dd, $H_a$ $CH_2$-Ph), $H_b$ $CH_2$-Ph), 2.19 (s, $CH_3$); NMR $^{13}C$: sugar: δ 109.1 ($C_{Ip}$), 74.5 (C-2'), 65.6 (C-3'), 54.7 (C-1'), 26.2 ($CH_3$), 25.1 ($CH_3$); heterocycle: δ 170.0 (C-4), 145.1 (C-2), 139.2 (C-6), 129.1 (C-3), 110.4 (C-5), 11.7 ($CH_3$). IR (KBr): 3130, 1630 $cm^{-1}$. UV (MeOH): $\lambda_{max}$=298 nm. log ε=3.03.

EXAMPLE 12

Synthesis of the 1-(1',2'-O-isopropylidene-α-D-xylofuranose-5-yl)-2-methyl-3-hydroxypyridine-4-(1H)-one (known as: 2-methyl-3-hydroxypyridine-4-(1H)-one of mono-acetone xylose) (12)

The 2-methyl-3-hydroxypyridine-4-(1H)-one of mono-acetone xylose is prepared according to the method described in example 9. Starting from 1.00 g (2.58 mmol) of 2-methyl-3-benzyloxypyridine- 4-(1H)-one of mono-acetone xylose, after extraction and re-crystallization in a hexane-acetone mixture, 545 mg (1.83 mmol) of 2-methyl-3-hydroxypyridine-4-(1H)-one of mono-acetone xylose is isolated, which is pure at chromatographic and NMR analyses. Yield: 71%.

12

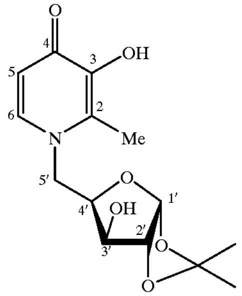

white powder
F = 233° C.
Rf = 0.21 (Ph—H—MeOH; 4:1)

NMR $^1H$: sugar: δ 5.87 (d,$J_{1',2'}$=3.5 Hz, H-1'), 4.46 (d,J2',3'=3.8 Hz, H-2'), 4.22–4.05 (massive, H-3', H-4', H-5'), 1.33 ($CH_3$), 1.21 (s, $CH_3$); heterocycle: δ 7.57 (d, J5,6=9.3 Hz, H-6), 6.14 (d, H-5), 2.30 (s, $CH_3$); NMR $^{13}C$: sugar: δ 110.7 ($C_{Ip}$), 104.3 (C-1'), 84.7 (C-2'), 79.6 (C-3'), 73.5 (C-4'), 51.6 (C-5'), 26.5 ($CH_3$), 25.9 ($CH_3$); heterocyle: δ 169.9 (C-4), 145.1 (C-2), 13 9.9 (C-6), 129.2 (C-3), 110.7 (C-5) 12.2 ($CH_3$). IR (KBr): 3178, 1635 $cm^{-1}$. UV (MeOH): $\lambda_{max}$=298 nm. log ε=3.04.

EXAMPLE 13

Synthesis of the 1-(1',2':3',4'-di-O-isopropylidene-α-D-galactopyranose-6-yl)-2-methyl-3-hydroxypyrdine-4(1H)-one (known as: 2-methyl-3-hydroxypyridine-4(1H)-one of diacetone galactose) (13)

The 2-methyl-3-hydroxypyridine-4(1H)-one of di acetone galactose is prepared according to the method described in example 9. Starting from 900 mg (1.97 mmol) of 2-methyl-3-benzyloxypyridine-4(1H)-one of diacetone gal actose, after extraction and re-crystallization in a hexane-acetone mixture, 521 mg (1.42 mmol) of 2-methyl-3-hydroxypyridine-4(1H)-one of diacetone galactose is isolated, which is pure at chromatographic and NMR analyses. Yield: 72%.

13

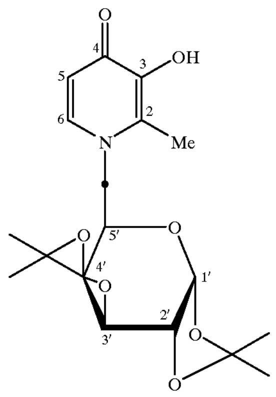

brown powder
$[\alpha]^{25}_D$ = -60° (c = 0.9; MeOH)
F = 90° C.
Rf = 0.29 (Ph—H—MeOH; 4:1)

NMR $^1H$: sugar: δ 5.41 (d, $J_{1',2'}$=4.9 Hz, H-1'), 4.64 (dd, $J_{3',4'}$=7.7 Hz, H-3'), 4.33 (dd, $J_{4',5'}$=7.7 Hz H-4'), 4.25 (dd, J2',3'=2.19 Hz, H-2'), 4.08 (m, H-$6_a$) 3.98 (m, H-5'), 3.87 (dd, H-$6'_b$), 1.38 ($CH_3$),1.29 (s, 2×$CH_3$), 1.22 (s, $CH_3$); heterocycle: δ 7.61 (d, J5,6=7.3 Hz, H-6), 6.15 (d, J5,6=7.4 Hz, H-5), 2.22 (s, $CH_3$); NMR $^{13}C$: sugar: δ 108.7 ($C_{Ip}$), 107.9 ($C_{Ip}$), 95.5 (C-1'), 70.4 (C-2'), 70.1 (C-3'), 69.5 (C-4'), 67.2 (C-5'), 52.3 (C-6'), 25.9 ($CH_3$), 25.6 ($CH_3$), 25.6 ($CH_3$), 24.6 ($CH_3$), 24.3 ($CH_3$); heterocycle: δ 168.7 (C-4), 145.3 (C-2), 137.8 (C-6), 129.8 (C-3), 110.5 (C-5), 11.6 ($CH_3$). IR (KBr): 3176, 1632 $cm^{-1}$. UV (MeOH): $\lambda_{max}$=298 nm. log ε=3.04.

EXAMPLE 14

Synthesis of the 1-glyceryl-2-methyl-3-hydroxypyridine-4(1H)-one (known as: 2-methyl-3-dydroxypyridine-4(1H)-one of glycerol) (14)

4.2 g (14.5 mmol) of 2-methyl-3-benzyloxypyridine-4 (1H)-one of glycerol is put into the mixture of 54 mL ethanol—6 mL $H_2O$, and 0.11 g of Pd/C at 10% is added. The reaction medium is subjected to catalytic hydrogenolysis under agitation at room temperature for 24 hours. At the end of this hydrogenolysis, the reaction medium is filtered. The filtered Pd/C is washed with EtOH; then the filtrate is evaporated under reduced pressure. The solid residue is re-crystallized in a MeOH-ethyl acetate mixture to obtain 2.05 g (10.3 mmol) of 2-methyl-3-hydroxypyridine-4(1H)-one of glycerol, which is pure at chromatographic and NMR analyses. Yield: 71%.

14

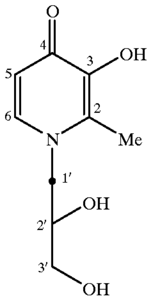

white powder

F = 179° C.

Rf = 0.1 (Ph—H—MeOH; 4:1)

NMR $^{1}H$: sugar: δ 4.15 (d,$J_{1'a,1'b}$=13.7 Hz, H-1'$_a$), 3.74 (dd, $J_{1'b,2}$=8.7 Hz H-1'$_b$), 3.67 (massive, H-2'), 3.42 (dd, $C_{3'a,3'b}$=10.7 Hz, $J_{3'a,2'}$=4.2 Hz, $Hz_{3'a}$) 3.30 (dd, $J_{3'b,2'}$=6.4 Hz, $H_{3'b}$); heterocycle: δ 7.47 (d, J5,6=7.35 Hz, H-6), 6.11 (d, H-5), 2.30 (s, $CH_3$); NMR $^{13}C$: sugar: δ 70.6 (C-2'), 63.2 (C-3'), 55.7 (C-1'); heterocycle: δ 168.8 (C-4), 145.1 (C-2), 138.5 (C-6), 129.3 (C-3), 110.1 (C-5), 11.6 ($CH_3$). IR (KBr): 3130, 1630 $cm^{-1}$. UV (MeOH): $\lambda_{max}$=298 nm. log ϵ=3.03.

EXAMPLE 15

Synthesis of the 1-(2',4':3',5'-di-O-methylene-xylityl)-2-methyl-3-hydroxypyridine-4(1H)-one (known as: 2-methyl-3-hydroxypyridine-4(1H)-one of dimethylene xylitol) (9) by hydrogenolysis in acid environment 1.00 g (2.68 mmol) of 2-methyl-3-benzyloxypyridine-4(1H)-one of dimethylene xylitol compound is put into a mixture of 10 mL ethanol—2 mL $H_2O$; then 0.08 g of Pd/C at 10% is added, and the pH of the solution is adjusted to pH=1 with a solution of concentrated HCl. The reaction medium is then subjected to catalytic hydrogenolysis under agitation at room temperature for 4 hours. At the end of this hydrogenolysis, the reaction medium is filtered. Then, 25 mL of water is added to the residue, and the solution is neutralized by addition of an aqueous solution of soda. The reaction medium is extracted with 2×20 mL of dichloromethane; the organic phases are collected, dried on sodium sulphate, filtered, and evaporated under reduced pressure; 509 mg (1.80 mmol) of 2-methyl-3-hydroxypyridine-4(1H)-one of dimethylene xylitol is isolated, which is pure at chromatographic and NMR analyses. Yield: 67%.

The physical constants are identical to those described in example 9.

EXAMPLE 16

Synthesis of the 1-glyceryl-2-methyl-3-hydroxypyridine-4(1H)-one (known as: 2-methyl-3-hydroxypyridine-4(1H)-one of glycerol) (14) by hydrogenolysis in acid environment The 2-methyl-3-hydroxypyridine-4(1H)-one of glycerol is prepared starting from the 2-methyl-3-hydroxypyridine-4(1H)-one of solketal according to the method described in example 15. The extraction and purification protocol is the following: filtration of the catalyst, addition of water, followed by elimination of the organic solvent, lyophilization, retake-up of the residue by an organic solvent, neutralization using Dowex $OH^-$ resin, filtration, and finally evaporation of the solvent. Starting from 1.00 g (3.04 mmol) of 2-methyl-3-benzyloxypyridine-4(1H)-one of solketal, 790 mg (2.73 mmol) of 2-methyl-3-hydroxypyridine-4(1H)-one of glycerol is isolated, which is pure at chromatographic and NMR analyses. Yield: 90%.

The physical constants are identical to those described in example 14.

EXAMPLE 17

Synthesis of the 1-xylityl-2-methyl-3-hydroxypyridine-4(1H)-one (known as: 2-methyl-3-dydroxypyridine-4(1H)-one of xylitol) (17) by hydrogenolysis in acid environment The 2-methyl-3-hydroxypyridine-4(1H)-one of xylitol is prepared starting from the 2-methyl-3-hydroxypyridine-4(1H)-one of diacetone xylitol (2) according to the method described in example 16. Starting from 10.1 g (23.5 mmol) of 2-methyl-3-benzyloxypyridine-4(1H)-one of diacetone xylitol, 4.25 g (16.3 mmol) of 2-methyl-3-hydroxypyridine-4(1H)-one of xylitol is isolated, which is pure at chromatographic and NMR analyses. Yield: 69%.

17

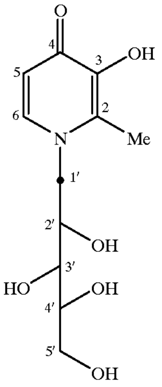

white powder

F = 184° C.

NMR $^{13}C$: sugar: δ 71.2–70.9 (C-2'-C-4'), 62.4 (C-5'), 55.7 (C-1'); heterocycle: δ 168.8 (C-4), 144.9 (C-2), 141.0 (C-3), 138.4 (C-6), 110.1 (C-5), 11.6 ($CH_3$).

EXAMPLE 18

Complexation with $Fe^{III}$

The complexation with regard to $Fe^{III}$ of the different ligands was studied on a JASCO V-530 spectrophotometer driven by a microcomputer equipped with programs for acquisition and analysis, the chelating properties of 2-methyl-3-hydroxypyridine-4(1H)-one of solketal (11), 2-methyl-3-hydroxypyridine-4(1H)-one of glycerol (14), 2-methyl-3-hydroxypyridine-4(1H)-one of diacetone xylitol (10), 2-methyl-3-hydroxypyridine-4(1H)-one of xylitol (17), and 2-methyl-3-hydroxypyridine-4(1H)-one of mono-acetone xylose (12) were compared to those of the 1.2-dimethyl-3-hydroxypyridine-4(1H)-one (known as: Deferiprone or L1) using a UV spectrophotometric method.

The samples were prepared as follows:

- preparation of solutions of ligands in $H_2O$ at the concentration of $3.6\times10^{-3}$ M.
- preparation of an aqueous solution of $Fe^{III}$ at $1.2\times10^{-3}$ M, starting from $FeCl_3.6\ H_2O$.

The sample range is obtained by the mixture of the two solutions of ligands in the following proportions:

| |
|---|
| 1 mL of $FeCl_3$ at 1.2 × $10^{-3}$ M + 0.2 mL of ligand at 3.6 × $10^{-3}$ M + 0.8 mL of $H_2O$ |
| 1 mL of $FeCl_3$ at 1.2 × $10^{-3}$ M + 0.6 mL of ligand at 3.6 × $10^{-3}$ M + 0.4 mL of $H_2O$ |
| 1 mL of $FeCl_3$ at 1.2 × $10^{-3}$ M + 0.7 mL of ligand at 3.6 × $10^{-3}$ M + 0.3 mL of $H_2O$ |
| 1 mL of $FeCl_3$ at 1.2 × $10^{-3}$ M + 0.8 mL of ligand at 3.6 × $10^{-3}$ M + 0.2 mL of $H_2O$ |
| 1 mL of $FeCl_3$ at 1.2 × $10^{-3}$ M + 1 mL of ligand at 3.6 × $10^{-3}$ M |

As a result, the sample range obtained presents the following respective values of Rv: 0.2; 0.4; 0.6; 0.7; 0.8; 1. Since the solubility of the 2-methyl-3-hydroxypyridine-4(1H)-one of diacetone xylitol (10) in water is weak, its complexation with regard to $Fe^{III}$ was evaluated starting from an aqueous solution of chlorohydrate at $3.6\times10^{-3}$ M. The latter was obtained by addition of a stoichiometric quantity of HCl.

The spectra of the solutions of ligand on the one hand, and of $FeCl_3$ on the other, present a single absorption peak and are characterized by:

Deferiprone® and derivatives 10–12, 14 and 17: $\lambda_{max}$= 293–296 nm;

$FeCl_3$: $\lambda_{max}$ =302 nm.

Chelation is instantaneous and results in the appearance of a purple colouring starting right from the mixture of the two solutions; the solutions remain clear, and no precipitation is observed.

Figure 9:
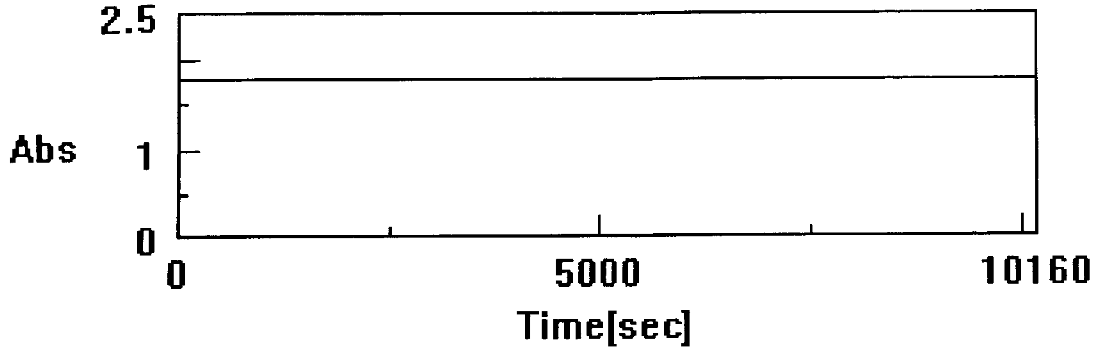
FIG. 9 represents the variation of OD as a function of time for 1,2-dimethyl-3-hydroxypyridine-4(1H)-one of solketal.

A control of the optical density (OD) in the course of time (plate outside text, FIG. 9) highlights the stability of the complex, as well as its immediate and quantitative formation. The spectra of the different mixtures indicate the appearance of an absorption maximum at a $\lambda_{max}$ close to 500 nm.

Whatever the nature of the ligand, the OD curve=f(Rv) obtained may be assimilated to a straight line in the range of R of between 0 and 0.7 (plates outside text, FIGS. 1 to 8) With the exception of the 2-methyl-3-hydroxypyridine-4(1H)-one of xylitol (17) (plate outside text No. 8 of 16), beyond the ratio Rv=0.7, the curve evolves towards an asymptote with OD values generally greater than 1.5.

Figure 5:
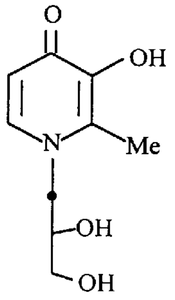
FIG. 5 represents the variation of OD as a function of Rv for 1,2-dimethyl-3-hydroxypyridine-4(1H)-one of glycerol after 1:10 dilution.
Figure 5:
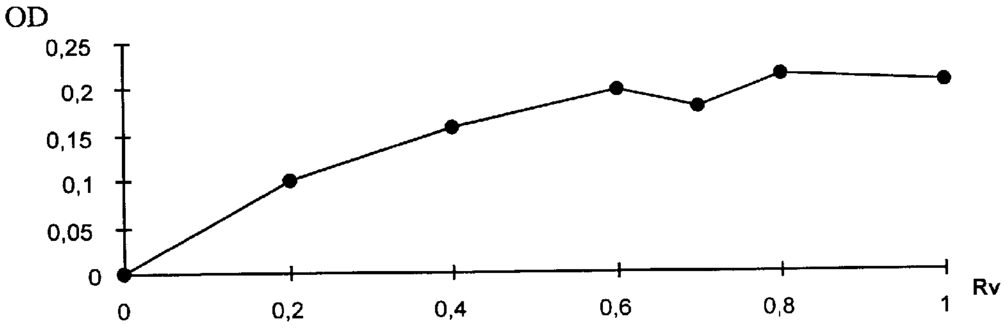
Figure 5:
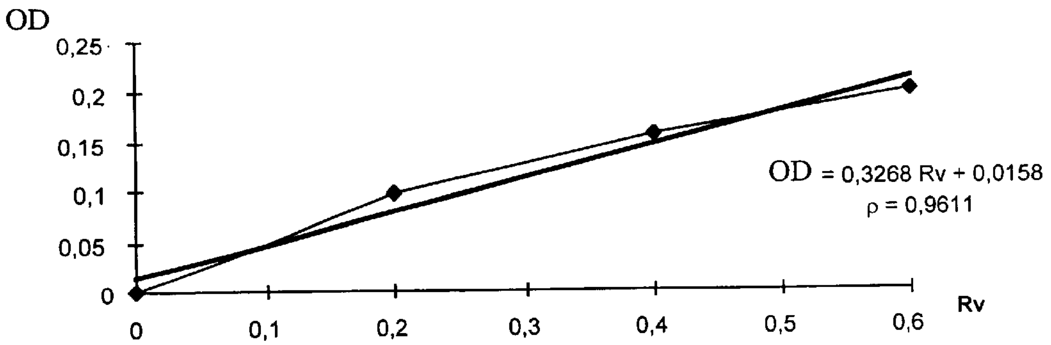
Figure 6:
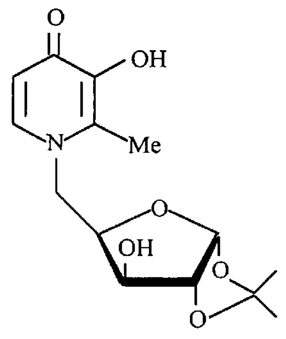
FIG. 6 represents the variation of OD as a function of Rv for 1,2-dimethyl-3-hydroxypyridine-4(1H)-one of monoacetone xylose.
Figure 6:
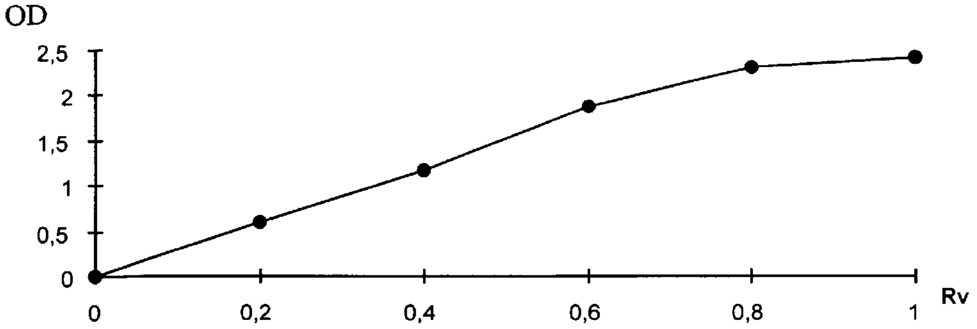
Figure 6:
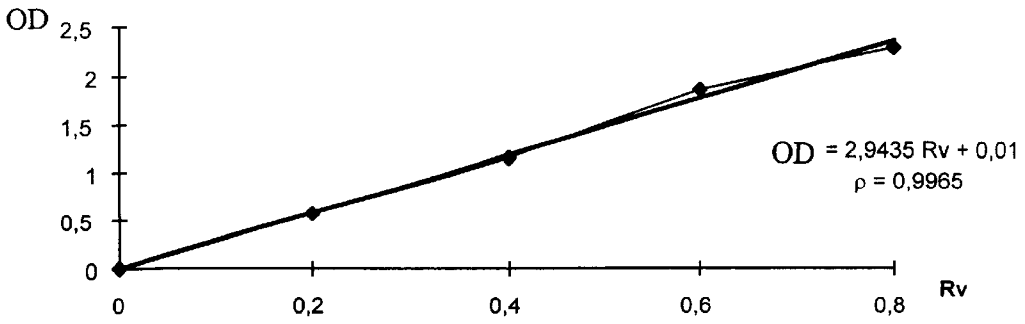
Figure 7:
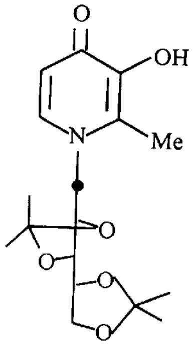
FIG. 7 represents the variation of OD as a function of Rv for 1,2-dimethyl-3-hydroxypyridine-4(1H)-one of diacetone xylitol.
Figure 7:
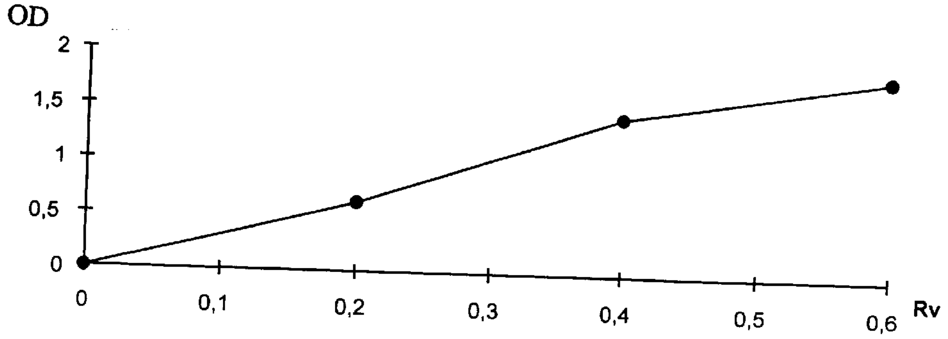
Figure 7:
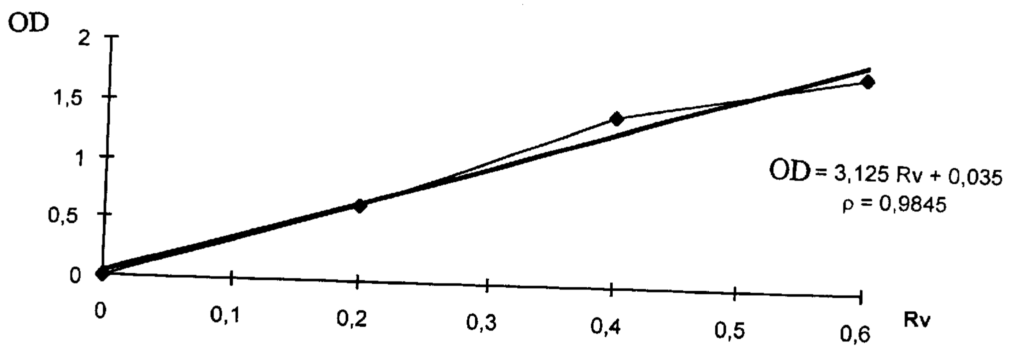
Figure 8:
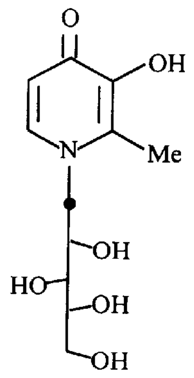
FIG. 8 represents the variation of OD as a function of Rv for 1,2-dimethyl-3-hydroxypyridine-4(1H)-one of xylitol.
Figure 8:
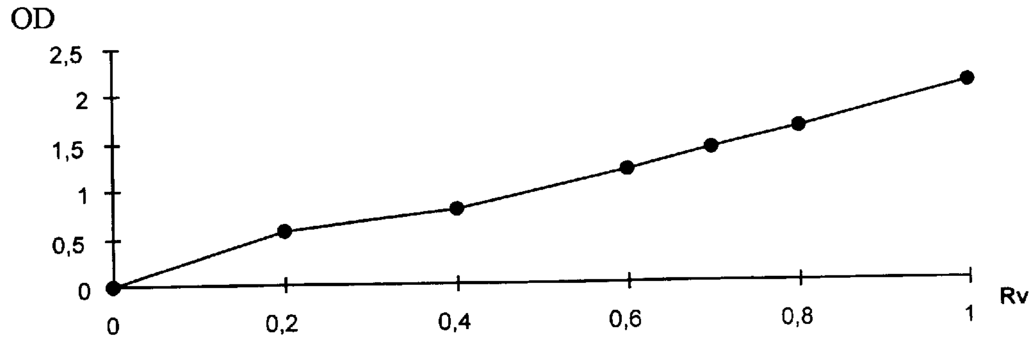
Figure 8:
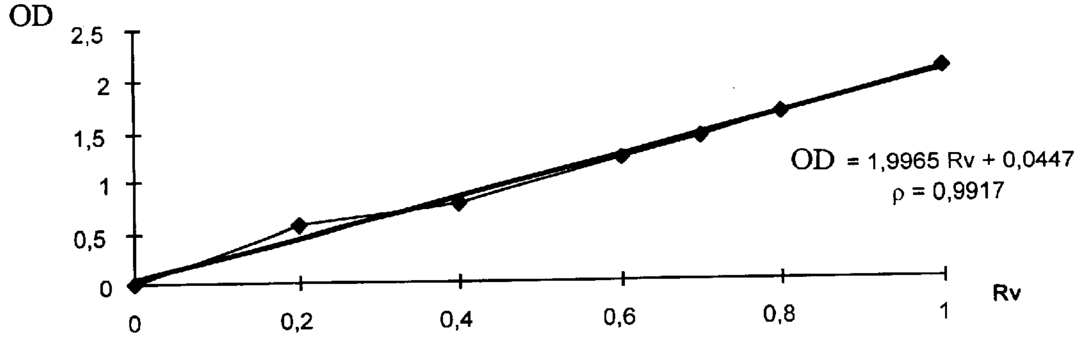

This quasi-horizontal portion of curve cannot be put down to the high values of OD found beyond Rv=0.6 because the diagram obtained after dilution of the samples at 1:10 is practically identical to the values of OD, and maintains the same appearance (examples of $L_1$ (plate outside text, FIG. 2) and 2-methyl-3-hydroxypyridine-4(1H)-one of glycerol (14) (plate outside text. FIG. 5)).

This asymptotic phenomenon is not found for 2-methyl-3-hydroxypyridine-4(1H)-one of xylitol which presents a linear variation for the set of values of Rv ranging between 0 and 1, the equations of the straight lines obtained for the set of products are gathered together in the table that follows.

| Ligand | Straight-line equation | Domain of calcul. |
|---|---|---|
| 1.2-dimethyl-3-hydroxypyridine-4(1H)-one | OD = 3.034 Rv − 0.027<br>ρ = 0.995 | 0 < Rv < 0.6 |
| 2-methyl-3-hydroxypyridine-4(1H)-one of diacetone xylitol (10) | OD = 3.125 Rv + 0.035<br>ρ = 0.984 | 0 < Rv < 1 |
| 2-methyl-3-hydroxypyridine-4(1H)-one of xylitol (17) | OD = 1.996 Rv + 0.044<br>ρ = 0.992 | 0 < Rv < 1 |
| 2-methyl-3-hydroxypyridine-4(1H)-one of solketal (11) | OD = 3.189 Rv − 0.110<br>ρ = 0.988 | 0 < Rv < 0.7 |
| 2-methyl-3-hydroxypyridine-4(1H)-one of glycerol (14) | OD = 3.315 Rv − 0.032<br>ρ = 0.996 | 0 < Rv < 0.6 |

-continued

| Ligand | Straight-line equation | Domain of calcul. |
|---|---|---|
| 2-methyl-3-hydroxypyridine-4(1H)-one of mono-acetone xylose (12) | 0D = 2.943 Rv + 0.010<br>ρ = 0.996 | 0 < Rv < 1 |

EXAMPLE 19

Acute Toxicity in Mice

The acute toxicity of compounds 10–12, 14 and 17, as well as that of L1, were evaluated in mice.

The samples are put in a solution either in water or in a mixture of water-DMSO (3:2; v/v) so as to obtain solutions of varying concentrations, either lower than or equal to 130 $g\cdot L^{-1}$; the volumes injected are calculated on the basis of 0.2 mL for a mouse body weight of 20 g.

The 1.2-dimethyl-3-hydroxypyridine-4(1H)-one (L1) was solubilized in the form of chlorohydrate. The toxicity is evaluated starting from aqueous solutions, either buffered or not with $NaH_2PO_4$ or else with $Na_2HPO_4$, or else after addition of a stoichiometric quantity of $NaHCO_3$.

The 2-methyl-3-hydroxypyridine-4(1H)-one derivatives of glycerol (14), of xylitol (17), of mono-acetone xylose (12) and of solketal (11) were injected by I. V. route.

The 2-methyl-3-hydroxypyridine-4(1H)-one compound of diacetone xylitol (10) was injected by I. P. route.

The results gathered together in the table below show that:

- the 2-methyl-3-hydroxypyridine-4(1H)-one of glycerol (14), which presents a solubility of over 130 $g\cdot L^{-1}$ in water, is non-toxic at 1300 $mg\cdot kg^{-1}$, unlike L1, which induces a mortality of 100% at this dose;
- the 2-methyl-3-hydroxypyridine-4(1H)-one of solketal (11), presents a toxicity higher than that of L1 and induces adverse neurophysiological effects;
- the 2-methyl-3-hydroxypyridine-4(1H)-one of xylitol (17) and the 2-methyl-3-hydroxypyridine-4(1H)-one of mono-acetone xylose (12) present the first toxic effects at 1300 $mg\cdot kg^{-1}$ (=LD10) and thus prove less toxic than L1;
- the 2-methyl-3-hydroxypyridine-4(1H)-one of diacetone xylitol (10) presents a weaker toxicity than L1, but is less soluble at the doses studied.

| Compounds | Sex | Acute toxicity in mice LD50 ± SD |
|---|---|---|
| L1 chlorohydrate 1.2-dimethyl-3-hydroxypyridine-4(1H)-one | M | 783 ± 50 $mg.kg^{-1}$ |
| | F | 868 ± 86 $mg.kg^{-1}$ |
| 2-methyl-3-hydroxypyridine-4(1H)-one | M | totally innocuous at 1300 $mg.kg^{-1}$ |

-continued

| Compounds | Sex | Acute toxicity in mice LD50 ± SD |
|---|---|---|
| of glycerol (14) | F | (maximum solubility) |
| 2-methyl-3-hydroxypyridine-4(1H)-one | M | totally innocuous at 1000 $mg.kg^{-1}$ |
| of xylitol (17) | F | (maximum solubility) |
| 2-methyl-3-hydroxypyridine-4(1H)-one | M | totally innocuous at 1300 $mg.kg^{-1}$ |
| of mono-acetone xylose (12) | F | LD10 = 1000 $mg.kg^{-1}$ |

-continued

| Compounds | Sex | Acute toxicity in mice LD50 ± SD |
|---|---|---|
| 2-methyl-3-hydroxypyridine-4(1H)-one | M | 817 ± 75 $mg.kg^{-1}$ |
| of solketal (11) | F | 745 ± 84 $mg.kg^{-1}$ |
| 2-methyl-3-hydroxypyridine-4(1H)-one | M | >650 $mg.kg^{-1}$ (I. P.) |
| of diacetone xylitol (10) | F | |

TABLE I-A

Acute toxicity of the chlorohydrate of 1.2-dimethyl-3-hydroxypyridine-4(1H)-one (L1) by I.V. route in female mice

| Dose (mg/kg) | Solvent (0.2 mL/20 g) | pH | No. of mice | Secondary effects | ✞ | Mortality times |
|---|---|---|---|---|---|---|
| 1300[b] | water | 2.0 | 3 | irritation at injection, tetany | 3 | 20 sec., 10 sec., 10 sec. |
| 650[b] | water | 2.1 | 5 | convulsions (8/8) | 5 | 54 sec., 30 sec., 20 sec., 25 sec., 26 sec. |
| 325[b] | water | 2.5 | 5 | irritation at injection, spontaneous decrease in activity 2–4 min. (5/5) | 0 | — |
| 650[c] | aq.$NaHCO_3$ | 7 | 5 | spontaneous decrease in activity xx min. before death (5/5) | 5 | 5 h 45, 6 h, 5 h, 4 h, 5 h 45 |
| 650[b] | $Na_2HPO_4$ buffer | 3 | 3 | irritation at injection, tetany | 3 | 50 sec., 30 sec., 35 sec. |
| — | $Na_2HPO_4$ buffer | 3 | 3 | shock, convulsions (6/6) | 3 | 50 sec., 50 sec., 45 sec. |
| 1300 | $Na_2HPO_4$ buffer | 4 | 5 | irritation at injection. | 5 | 3 min., 4 min., 4 min., 5 min., 7 min. |
| 1050 | $Na_2HPO_4$ buffer | 4 | 10 | spontaneous decrease in activity xx min. before death, with convulsions | 9 | 3 min., 6 min., 7 min., 9 min., 1 h, 3 h, 4 h, 5 h, 6 h |
| 850 | $Na_2HPO_4$ buffer | 4 | 10 | | 5 | 3 min., 3 min., 5 min., 5 h, 5 h |
| 650 | $Na_2HPO_4$ buffer | 4 | 10 | | 2 | 1 h. 5 h |
| 525 | $Na_2HP0_4$ buffer | 4 | 5 | | 0 | — |
| — | $Na_2HPO_4$ buffer | 4 | 5 | irritation at injection (5/5) | 0 | — |

✞Mortality
[a]Doses calculated in L1 equivalent (1.65 $g.kg^{-1}$ of chlorohydrate of L1 corresponding to 1.30 $g.kg^{-1}$ of L1).
[b]Filtered solutions injected I.V.
[c]Non-filtered solutions injected I.P.

TABLE 1-B

Acute toxicity of the chlorohydrate of 1.2-dimethyl-3-hydroxypyridine-4(1H)-one (L1) by I.V. route in male mice

| Dose (mg/kg) | Solvent (0.2 mL/20 g) | pH | No. of mice | Secondary effects | ✞ | Mortality times |
|---|---|---|---|---|---|---|
| 1300 | $Na_2HPO_4$ buffer | 4 | 5 | irritation at injection, | 5 | 3 min., 3 min., 3 min., 6 min., 8 min. |
| 1050 | $Na_2HPO_4$ buffer | 4 | 10 | spontaneous decrease in activity xx min. before death with convulsions | 10 | 3 min., 3 min., 6 min., 7 min., 7 min., 10 min., 1 h. 1 h. 2 h. 2 h |
| 850 | $Na_2HPO_4$ buffer | 4 | 10 | | 5 | 6 min., 7 min., 7 min., 5 h. 5 h |

TABLE 1-B-continued

Acute toxicity of the chlorohydrate of 1.2-dimethyl-3-hydroxypyridine-4(1H)-one (L1) by I.V. route in male mice

| Dose (mg/kg) | Solvent (0.2 mL/20 g) | pH | No. of mice | Secondary effects | ✝ | Mortality times |
|---|---|---|---|---|---|---|
| 650 | $Na_2HPO_4$ buffer | 4 | 10 | | 2 | 12 min., 5 h |
| 525 | $Na_2HPO_4$ buffer | 4 | 5 | | 0 | — |
| — | $Na_2HPO_4$ buffer | 4 | 5 | | 0 | — |

✝Mortality
[a]Doses calculated in L1 equivalent (1.65 $g.kg^{-1}$ of chlorohydrate of L1 corresponding to 1.30 $g.kg^{-1}$ of L1).
[b]Filtered solutions injected I.V.

TABLE 2

Acute toxicity of the 2-methyl-3-hydroxypyridine-4(1H)-one of glycerol (14) by I.V. route in mice

| Dose (mg/kg) | Solvent (0.2 mL/20 g) | No. of mice | Secondary effects | ✝ | Mortality times | Sex |
|---|---|---|---|---|---|---|
| 1300* | water | 5 | none (5/5) | 0 | — | M |
| 1300* | water | 5 | none (5/5) | 0 | — | F |
| 1300 | water 60/DMSO 40 | 5 | none (5/5) | 0 | — | M |
| 1300 | water 60/DMSO 40 | 5 | none (4/5)[a] | 0 | — | F |
| — | water 60/DMSO 40 | 5 | 1 min. of dyspnoea | 0 | — | M |
| — | water 60/DMSO 40 | 5 | appearing 30 sec. after injection (5/5) | 0 | — | F |

✝Mortality
*Filtered solution
[a]The only secondary effect observed in one mouse was due to DMSO.

TABLE 3

Acute toxicity of the 2-methyl-3-hydroxypyridine-4(1H)-one of xylitol (17) by I.V. route in mice

| Dose (mg/kg) | Solvent (0.2 mL/20 g) | No. of mice | Secondary effects | ✝ | Mortality times | Sex |
|---|---|---|---|---|---|---|
| 650* | water | 5 | none (5/5) | 0 | — | M |
| 650* | water | 5 | none (5/5) | 0 | — | F |
| 1000* | water | 5 | none (5/5) | 0 | — | M |
| 1000* | water | 5 | none (5/5) | 0 | — | F |
| 1000* | water 60/DMSO 40 | 5 | 1 min. of dyspnoea appearing | 0 | — | M |
| 1000* | water 60/DMSO 40 | 5 | 30 sec. after injection (20/20) | 0 | — | F |
| 1300* | water 60/DMSO 40 | 5 | transient reduction in | 0 | — | M |
| 1300* | water 60/DMSO 40 | 5 | spontaneous activity[a] | 0 | — | F |

✝Mortality
*Filtered solution
[a]The spontaneous activity started to decrease significantly in general 2 hours after injection. This abnormal behaviour appeared in general within the following 5 hours (20/20).

TABLE 4

Acute toxicity of the 2-methyl-3-hydroxypyridine-4(1H)-one of mono-acetone xylose (12) by I.V. route in mice

| Dose (mg/kg) | Solvent (0.2 mL/20 g) | No. of mice | Secondary effects | ✞ | Mortality times | Sex |
|---|---|---|---|---|---|---|
| 1000* | water 60/DMSO 40 | 5 | dyspnoea appearing 30 sec. | 0 | — | M |
| 1000* | water 60/DMSO 40 | 5 | after injection and continuing | 1 | 4 min. (respiratory deficiency) | F |
| 1000* (double dose) | water 60/DMSO 40 | 5 | between 1 and 3 min., whatever the dose | 0 | — | F |
| 1300 | water 60/DMSO 40 | 5 | used | 0 | — | M |
| 1300 | water 60/DMSO 40 | 5 | | 1 | between 6 and 18 h (death during night) | F |
| 1300 (double dose) | water 60/DMSO 40 | 5 | | 0 | — | F |

✞Mortality
*Filtered solution

TABLE 5

Acute toxicity of the 2-methyl-3-hydroxypyridine-4(1H)-one of solketal (11) by I.V. route in mice

| Dose (mg/kg) | Solvent (0.2 mL/20 g) | No. of mice | Secondary effects | ✞ | Mortality times | Sex |
|---|---|---|---|---|---|---|
| 500* | water 60/DMSO 40 | 5 | 1 min. phase of convulsive disorder | 0 | — | M |
| 500* | water 60/DMSO 40 | 5 | followed by 3 min. to 7 min. | 0 | — | F |
| 650* | water 60/DMSO 40 | 5 | of reduction in spontaneous | 1 | 3 min. | M |
| 650* | water 60/DMSO 40 | 5 | activity (30/30) | 0 | — | F |
| 800* | water 60/DMSO 40 | 5 | | 2 | 5, 4 min. | M |
| 800* | water 60/DMSO 40 | 5 | | 2 | 7, 7 min. | F |
| 1000* | water 60/DMSO 40 | 5 | 1 min. convulsive phase followed by | 4 | 1, 3, 6, 120 min. | M |
| 1000* | water 60/DMSO 40 | 5 | 10 min. of drop in spontaneous activity (10/10) | 4 | 1, 5, 5, 7 min. | F |
| 1300 | water 60/DMSO 40 | 5 | death preceded by a marked convulsive | 5 | 30 seconds to 90 sec. | M |
| 1300 | water 60/DMSO 40 | 5 | phase (10/10) | 5 | | F |

✞: Mortality
*: Filtered solution

TABLE 6

Acute toxicity of the 2-methyl-3-hydroxypyridine-4(1H)-one of diacetone xylitol (10) by I.V. route in mice

| Dose (mg/kg) | Solvent (0.2 mL/20 g) | No. of mice | Secondary effects | ✞ | Mortality times | Sex |
|---|---|---|---|---|---|---|
| 325[a] | water 60/DMSO 40 | | none (5/5)[c] | 0 | — | M |

TABLE 6-continued

Acute toxicity of the 2-methyl-3-hydroxypyridine-4(1H)-one of diacetone xylitol (10) by I.V. route in mice

| Dose (mg/kg) | Solvent (0.2 mL/20 g) | No. of mice | Secondary effects | ✞ | Mortality times | Sex |
|---|---|---|---|---|---|---|
| 325[a] | water 60/DMSO 40 | 5 | none (5/5)[c] | 0 | — | F |

TABLE 6-continued

Acute toxicity of the 2-methyl-3-hydroxypyridine-4(1H)-one of diacetone xylitol (10) by I.V. route in mice

| Dose (mg/kg) | Solvent (0.2 mL/20 g) | No. of mice | Secondary effects | ✝ | Mortality times | Sex |
|---|---|---|---|---|---|---|
| 650[a] | water 60/DMSO 40 | 5 | none (5/5)[c] | 0 | — | M |
| 650[a] | water 60/DMSO 40 | 5 | none (5/5)[c] | 0 | — | F |
| — | water 60/DMSO 40[b] | 5 | none (5/5)[c] | 0 | — | M |
| — | water 60/DMSO 40[b] | 5 | none (5/5)[c] | 0 | — | F |

✝ Mortality
[a]Non-filtered homogeneous syrupy liquid injected by I.P. route
[b]I.P. route
[c]No visceral organ presented macroscopic lesions in the mice sacrificed at end of study period.

What is claimed is:

1. A process for regiospecific synthesis of new 3-hydroxypyridine-4(1H)-one derivatives of general formula:

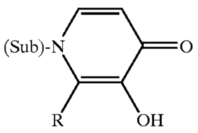

in which R represents an alkyl or alkylene or halo-alkyl or halo-alkylene radical, the halogens being chosen from among chloride and fluoride, linear or branched, having from 1 to 4 carbon atoms and having hetero-atoms or not, and Sub represents an itol, either cyclic or not, protected or not, starting from a 2-R-3-hydroxy pyran-4-one derivative and an amino itol, wherein said process comprises a first step (step a) of protection of the 3-hydroxy group of the pyranone derivative;

a second step (step b) of substitution of the intracyclic oxygen atom of the pyranone by the nitrogen atom of the amine function of the amino itol, to obtain the 2-R-3-hydroxypyridine-4(1H)-one derived from the itol, in which the protected pyranone obtained in step (a) is reached with the amino itol, in the presence of a strong base;

a third step (step c) of de-protection of the 3-OH group of the pyridinone cycle.

2. The process according to claim 1, wherein said itol is chosen from the group consisting of hexitol, pentitol, tetritol, glucitol, galactitol, mannitol, xylitol, erythritol, and glycerol.

3. The Process according to claim 1, wherein the step (a) aimed at protecting the 3-hydroxy group of the pyranone derivative comprises reacting the 2-R-3-hydroxypyran-4-one derivative with at least one molar equivalent of the P-X derivative, where P represents an alkyl group, either cyclic or not, branched or not, saturated or not, or else a phenyl group, either substituted or not, or else an aryl group, either substituted or not, and X is a leaving group, step (a) being carried out in the presence of at least 1 molar equivalent of a strong base chosen from among hydroxylated bases, or from among alcanoates and weak acid salts, where the cation is $Na^+$, $K^+$, $Li^+$, $Rb^+$, $Cs^+$, or else a cation of the alkaline-earth type, in a reaction solvent consisting of hydro-alcanolic mixtures, the alcanol being chosen from methanol, ethanol, propanol or isobutanol or else an alcanol alone, or else a polar aprotic solvent chosen from hexamethyl phosphorotriamide (HMPA), dimethyl formamide (DMF), dimethoxyethane (DME), dimethyl sulphoxide (DMSO), and acetone, or else a mixture of these, the polar aprotic solvent being associated or not with an apolar aprotic solvent chosen from the aromatic solvents, hydrocarbons or else ether oxides, or else a mixture of these solvents, step (a) comprising in addition the operations of elimination of the solvent and uptake of the residue by an organic solvent, subsequent washing of the organic phase with a basic aqueous solution as defined previously, and then with water and evaporation of the organic phases.

4. The process according to claim 3, wherein the group P is chosen from the group consisting of alkyl, benzyl and phenyl.

5. The process according to claim 3, wherein X is chosen from the group consisting of halides and sulphonates, chosen from chloride, bromide, iodide, tosylate, mesylate, brosylate, nosylate, and triflate.

6. The process according to claim 1 wherein the step (b) of substitution of the intracyclic oxygen atom of the pyranone by the nitrogen atom of the amino itol comprises reacting at least 1 molar equivalent of the protected pyranone obtained in step (a) with 1 molar equivalent of the amino itol in the presence of a strong base, as defined in step (a) according to claim 3 in a reaction solvent consisting of hydro-alcanol mixtures, the alcohol being chosen from methanol, ethanol, propanol, and isobutanol, or an alcanol alone, or a polar aprotic solvent chosen from among hexamethyl phosphorotriamide (HMPA), dimethyl formamide (DMF), dimethoxyethane (DME), dimethyl sulphoxide (DMSO), acetone, or else a mixture of these, the polar aprotic solvent being associated or not to an apolar aprotic solvent chosen from the aromatic solvents, hydrocarbons, or else ether oxides, or else a mixture of these solvents, step (b) further comprising the operations of neutralization of the base by addition of a mineral or organic acid, elimination of the organic solvent, up take of the residue by an organic solvent and washing of the organic phase with water, evaporation of the organic phase and purification of the residue by re-crystallization or chromatography.

7. The Process according to claim 1, wherein step (c) of de-protection of the pyridinone cycle of the compounds obtained from step (b), when P is chosen from benzyl, phenyl and allyl, by hydrogenolysis in the presence of a catalyst chosen from among Pd/C and any other hydrogenolysis catalyst chosen from platinum derivatives and nickel derivatives, in an alcanol, or else an alcanol-water mixture, the alcanol being chosen from among methanol, ethanol, propanol, isopropanol, or else an organic solvent associated or not to water and enabling solubilization of the de-protected product, chosen from tetrahydrofuran and dioxane, step (c) further comprising also the following operations of filtration of the catalyst, elimination of the organic solvent and purification of the residue by re-crystallization in a binary mixture of organic solvents, chosen from hexane and acetone.

8. The process according to claim 1, characterized in that step (c) of de-protection of the pyridinone cycle of the compounds obtained from step (b) may be carried out, when P is an allyl group, by acid catalyzed hydrolysis, after base catalyzed isomerization of the allyl group into a propenyl group, in the solvents or mixtures of solvents selected from the group consisting of an alcanol-water mixture, the alcanol being chosen from among methanol, ethanol, propanol, isopropanol or else an organic solvent associated or not to water.

9. Procedure according to claim 1, characterized in that step (c) of de-protection of the pyridinone cycle of the compounds obtained from step (b) may be carried out when P is an allyl group, by acid catalyzed hydrolysis, after base catalyzed isomerization of the allyl group into a propenyl group, in the solvents or mixtures of solvents described in claim 7.

10. Procedure according to claim 1, characterized in that the compounds obtained from step (c), the saccharide residue of which possesses protected hydroxyl groups, can undergo step (d) of de-protection according to the classic conditions on the basis of the nature of the protecting groups themselves.

11. A 2-R-3-hydroxypyridine-4(1H)-one itol derivative of the general formula:

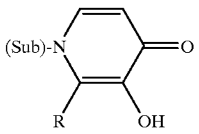

in which R represents an alkyl or alkylene, or halo-alkyl or halo-alkylene radical, having from 1 to 4 carbon atoms and having hetero-atoms or not, and Sub represents an itol chosen from the group consisting of hexitol, pentitol, tetritol, glucitol, galactitol, mannitol, xylitol, erythritol and glycerol.

12. 1-(2',3':4',5'-di-O-isopropylidene-xylityl)-2-methyl-3-benzyloxypyridine-4(1H)-one and 1-(2',3':4',5'-di-O-isopropylidene-xylityl)-2-methyl-3-hydroxypyridine-4(1H)-one.

13. 1-(2',4':3',5'-di-O-methylene-xylityl)-2-methyl-3-benzyloxypyridine-4(1H)-one and 1-(2',4':3',5'-di-O-methylene-xylityl)-2-methyl-3-hydroxypyridine-4(1H)-one.

14. 1-(2',3'-O-isopropylidene-glyceryl)-2-methyl-3-benzyloxypyridine-4(1H)-one and 1-(2',3'-O-isopropylidene-glyceryl)-2-methyl-3-hydroxypyridine-4(1H)-one.

15. 1-glyceryl-2-methyl-3-benzyloxypyridine-4(1H)-one.

16. 1-glyceryl-2-methyl-3-hydroxypyridine-4(1H)-one.

17. 1-xylityl-2-methyl-3-hydroxypyridine-4(1H)-one.

18. A medicament for the treatment of $Fe^{III}$ overload, comprising a therapeutically effective quantity of at least one compound according to claim 11 in a vehicle that may be administered to humans.

19. A therapeutic method for the treatment of haemoglobinopathies, β-thalassaemia or drepanocytosis comprises administering a therapeutically effective amount of at least one compound according to claim 11.

* * * * *